(12) United States Patent
Lukyanov et al.

(10) Patent No.: US 7,951,923 B2
(45) Date of Patent: May 31, 2011

(54) **FLUORESCENT PROTEINS AND CHROMOPROTEINS FROM NON-*AEQUOREA HYDROZOA* SPECIES AND METHODS FOR USING SAME**

(75) Inventors: Sergei Anatolievich Lukyanov, Moscow (RU); Dmitry Alexeevich Shagin, Moscow (RU); Yury Grigorievich Yanushevich, Moscow (RU)

(73) Assignee: Zakrytoe Aktsionernoe Obschestvo 'Evrogen', Moscow (RU)

( * ) Notice: Subject to any disclaimer, the term of this patent is extended or adjusted under 35 U.S.C. 154(b) by 610 days.

(21) Appl. No.: 10/532,681

(22) PCT Filed: Nov. 5, 2003

(86) PCT No.: PCT/RU03/00474
§ 371 (c)(1),
(2), (4) Date: Feb. 20, 2007

(87) PCT Pub. No.: WO2004/044203
PCT Pub. Date: May 27, 2004

(65) Prior Publication Data
US 2007/0298412 A1 Dec. 27, 2007

Related U.S. Application Data

(60) Provisional application No. 60/425,570, filed on Nov. 12, 2002, provisional application No. 60/429,795, filed on Nov. 27, 2002, provisional application No. 60/464,258, filed on Apr. 21, 2003, provisional application No. 60/480,080, filed on Jun. 20, 2003.

(51) Int. Cl.
C07H 21/02 (2006.01)
C07H 21/04 (2006.01)
C12P 21/06 (2006.01)

(52) U.S. Cl. ...................... 536/23.1; 435/69.1
(58) Field of Classification Search .............. 536/23.1; 435/69.1
See application file for complete search history.

(56) References Cited

U.S. PATENT DOCUMENTS

| 5,976,796 A | 11/1999 | Szalay et al. |
| 6,232,107 B1 | 5/2001 | Bryan et al. |
| 2008/0213879 A1* | 9/2008 | Baubet et al. .............. 435/325 |

FOREIGN PATENT DOCUMENTS

| CA | 2 331 882 | 1/2000 |
| JP | 10-234382 | 9/1998 |
| WO | 97/41228 | 11/1997 |
| WO | PCT/EP2001/007057 | * 6/2001 |
| WO | WO01/92300 | * 12/2001 |

OTHER PUBLICATIONS

Shagin et al., GFP-like proteins as ubiquitous metazoan superfamily: evolution of functional features and structural complexity, Mol Biol Evol. 21(5):841-50, 2004.*
Parmley et al., How do synonymous mutations affect fitness? Bioessays, 29(6): 515-9, 2007.*
Sample et al. et al., The structure and function of fluorescent proteins, Chem Soc Rev. 38(10):2852-64, 2009.*
Cubitt, AB., et al. "Understanding, Improving and Using Green Fluorescent Proteins" *Trends Biochem Sci.* (1995) vol. 20, No. 11, pp. 448-455, Abstract.
Patent Abstracts of Japan of JP 10-234382 dated Sep. 8, 1998 and English Computer-Generated Translation of Claims.
English Abstract of CA 2 331 882 dated Jan. 20, 2000.
Yang, et al., The Molecular Structure of Green Fluorescent Protein, Nature Biotechnology vol. 14. Oct. 1996, pp. 1246-1251.
Ormo et al., Crystal Structure of the *Aequorea victoria* Green Fluorescent Protein, Science, vol. 273, Sep. 6, 1996, pp. 1392-1395.
Matz et al., Fluorescent Proteins From Nonbioluminescent *Anthozoa* Species, Nature Biotechnology, vol. 17, Oct. 1999, pp. 969973.
Exhibit D: Alignment of Discloses Proteins and GFP, 2 Pages.
Heim et al., Engineering Green Fluorescent Protein for Improved Brightness, Longer Wavelengths and Fluorescence Resonance Energy Transfer, Current Biology, 1996, vol. 6. No. 2, pp. 178-182.
Siemering, et al., Mutations That Suppress the Thermosensitivity of Green Fluorescent Protein, Current Biology, 1996, vol. 6, No. 12, pp. 1653-1663.
Yang, et al., Improved Fluorescence and Dual Color Detection With Enhanced Blue and Green Variants of the Green Fluorescent Protein, The Journal of Biological Chemistry, vol. 273, No. 14 , pp. 8212-8216.
Wiedenmann et al. Cracks in the B-Can: Fluorescfent Proteins From *Anemonia sulcata* (Anthozoa, Actinaria) PNAS, Dec. 2000, vol. 97, No. 26, 14091-14096. Bevis et al. Rapidly Maturing Variants of the *Discosoma* Red Fluorescent Protein (DsRed) Nature Biotechnology, Jan. 2002, vol. 20, pp. 83-87.
Campbell et al., A Monomeric REF Fluorescent Protein, PNAS, Jun. 2002, vol. 99. No. 12, pp. 7877-7882.
Shaner et al., Improved Monomeric Red, Orange and Yellow Fluorescent Proteins Derived From *Discosoma* Sp. Red Fluorescent Protein, Nature Biotechnology Nov. 2004, pp. 1-6.

* cited by examiner

*Primary Examiner* — Wu-Cheng Winston Shen

(57) ABSTRACT

The present invention provides nucleic acid molecules encoding a fluorescent and chromo-proteins and mutants, variants and derivatives thereof, as well as proteins and peptides encoded by these nucleic acids. The nucleic acid molecules and proteins of interest are isolated from non-*Aequorea Hydrozoa* species. The proteins of interest include yellow fluorescent protein, phiYFP, from *Phialidium* sp., green fluorescent protein hydr1GFP and purple chromoprotein, hm2CP from hydroid medusae of sub-order Anthomedusae. Also of interest are proteins that are substantially similar to, or derivatives, or homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided. The subject protein and nucleic acid compositions find use in a variety of different applications and methods, particularly for labeling of biomolecules, cell or cell organelles. Finally, kits for use in such methods and applications are provided.

11 Claims, 9 Drawing Sheets

```
              10        20        30        40        50
GFP      MSKGEELFTGVVPILVELDGDVNGHKFSVSGEGEGDATYGKLTLKFICTTGKLPVPWPT
phiYFP   --S-AL--H-KL-YV--ME-N-D--T--IR-KY---SV--MDAQ-----DV----S
hydr1GFP   MT-T-QKKL-YKL----D-QT-K-I---V----T-VTEG-LV--E-EV-IS-VS
hm2CP    -EG-PA--QSDMTEKIFL--V--DQ--TLIAD-SSKFPH-DFNVHAV-E----MS-KP 60        70        80        90       100       110
GFP      LVTTFSYGVQCFSRYPDHMKQHDFFKSAMPEGYVQERTIFFKDDGNYKTRAEVKFEGDT
phiYFP     ---LT--A---AK--GPELK..--Y--G----------T-EG--VF----T--NGS
hydr1GFP -I-SL---AK--V---NEIN..----TF-S-H----K-TYEN--VLE-A-KLTM-SGA
hm2CP    ICHLIQ--EPF-AK--NGIS..H-AQECF----LTID--VR-EN--TMTSHHTYELD-TC 120       130       140       150       160       170
GFP      LVNRIELKGIDFKEDGNILGHKLEYNYNSHNVYIMADKQKNGIKVNFKIRHNIEDGSVQL..
phiYFP   VY--VK-N-QG---K--HV---KN--F--FTP-CL---WG-QANH-L-SA---M-E-TGSKEDFIV
hydr1GFP I----NV--TG-DK--HVCQKN--SSPP-TTYVV...PEGE--RLIYRNIYPTK--HYVV..
hm2CP    VIS-ITVNCDG-QP--P-MKDQ-VDILPTETHMEP..HGS-AVRQLCY-GITTA--GLMM..

180       190       200       210       220       230
GFP      ADHYQQNTPIGD.GPVLLPDNHYLSTQSALSKDPNEKRDHMVLLEFVTAAGITHGMDELYK
phiYFP   --T-M-----G---HV-EY-HETYHMT----VTDH--N-SFV-T-R-VDCRKTYL
hydr1GFP --TQ-V-R--RAQ-TSAI-TY-HLKSKVD--T--E-NK--ILK-TNC-FDADFS
hm2CP    SHFDSKL-FN-SRAIKI-GP-FVTVILKQM--TSD----VCQR-VLY-HSVPRITSAI
```

Fig. 1

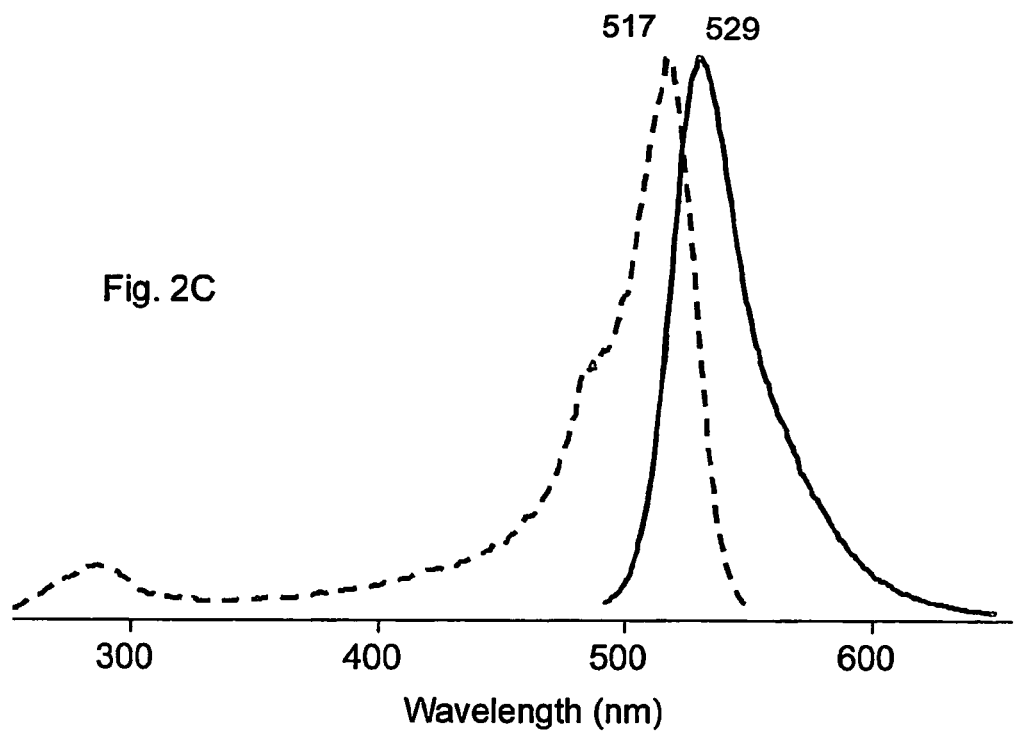
Fig. 2C
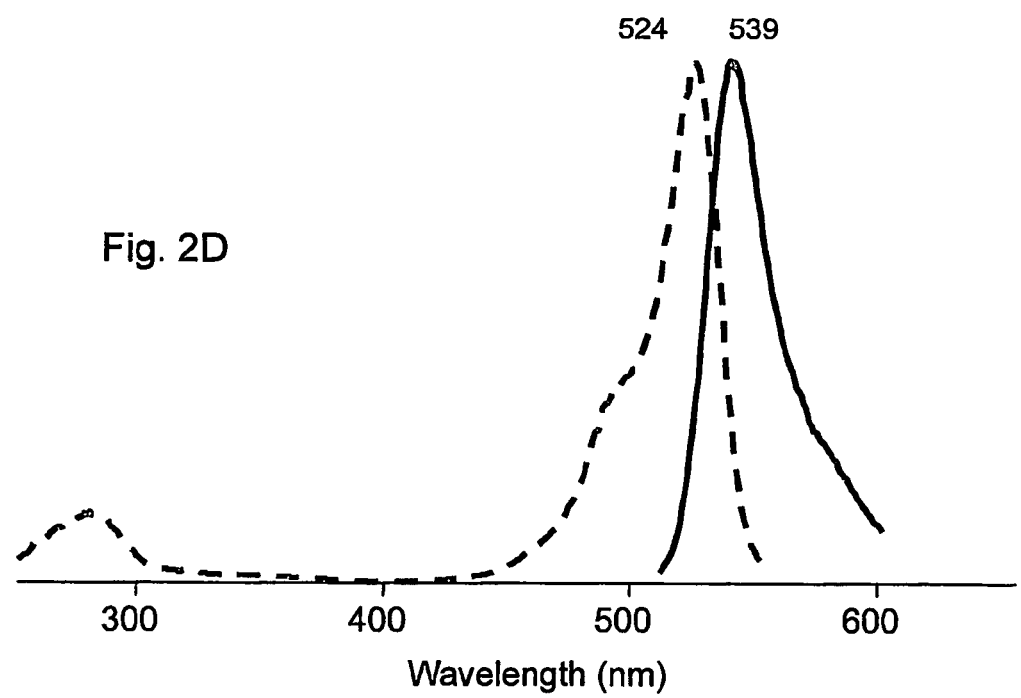
Fig. 2D
Fig. 2

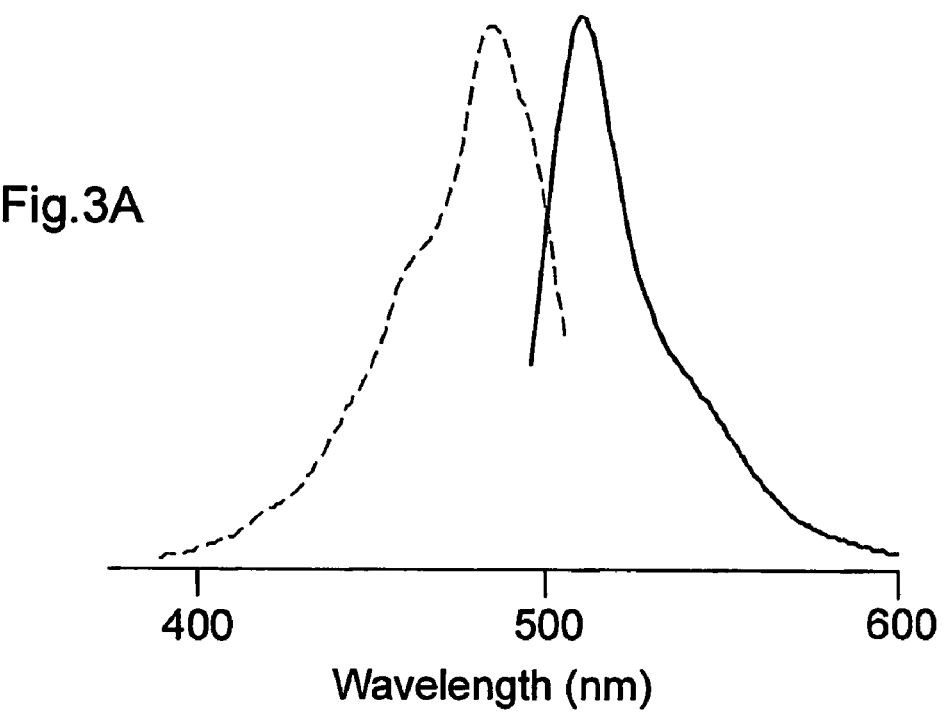
Fig.3A
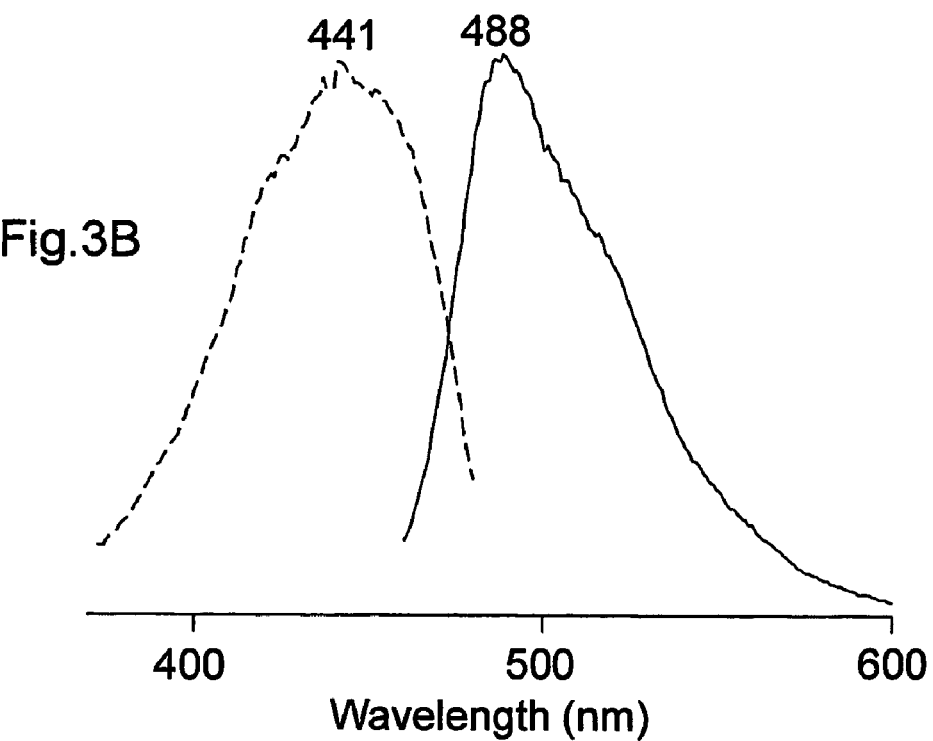
Fig.3B
Fig. 3

Fig.4A
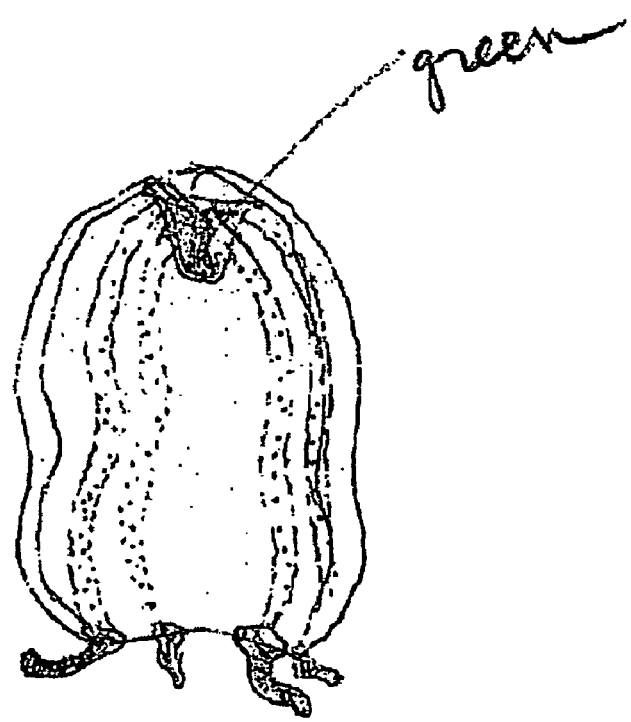
Fig.4B
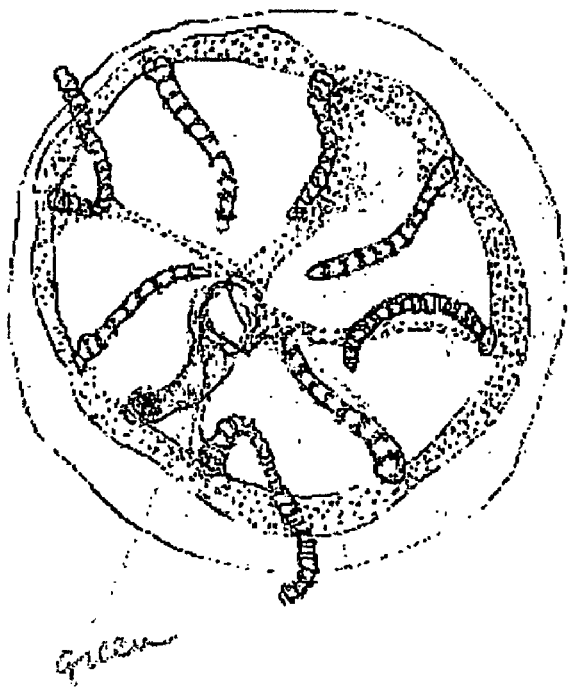
Fig. 4

FLUORESCENT PROTEINS AND CHROMOPROTEINS FROM NON-*AEQUOREA* *HYDROZOA* SPECIES AND METHODS FOR USING SAME This application claims the benefit of U.S. Provisional Application(s) Nos. 60/425,570 filed 12 Nov. 2002, 60/429,795 filed 27 Nov. 2002, 60/464,258 filed 21 Apr. 2003 and 60/480,080 filed 20 June 2003.

FIELD OF THE INVENTION

This invention relates generally to the field of biology and chemistry. More particularly, the invention is directed to fluorescent proteins.

BACKGROUND OF THE INVENTION

Labeling of a protein, cell, or organism of interest plays a prominent role in many biochemical, molecular biological and medical diagnostic applications. A variety of different labels have been developed and used in the art, including radiolabels, chromolabels, fluorescent labels, chemiluminescent labels, and the like, with varying properties and optimal uses. However, there is continued interest in the development of new labels. Of particular interest is the development of new protein labels, including fluorescent protein labels.

Green Fluorescent Protein (GFP), its mutants and homologs are widely known today due to their intensive use as in vivo fluorescent markers in biomedical sciences discussed in detail by Lippincott-Schwartz and Patterson in Science (2003) 300(5616):87-91). The GFP from hydromedusa *Aequorea aequorea* (synonym *A. victoria*), discovered by Johnson et al. in J Cell Comp Physiol. (1962), 60:85-104, was found as a part of bioluminescent system of the jellyfish where GFP played role of a secondary emitter transforming blue light from photoprotein aequorin into green light. Then, similar proteins were isolated from several bioluminescent coelenterates including hydroid medusa *Phialidium gregarium*, sea pansy *Renilla* (class Anthozoa) and others (see Ward et al. in Photochem. Photobiol. (1982), 35: 803-808; Levine et al. in Comp. Biochem. Physiol. (1982), 72B: 77-85; Chalfie in Photochem. Photobiol. (1995), 62:651-656). All these proteins display green fluorescent (emission at 497-509 nm) and functioned as the secondary emitters in bioluminescence. Fluorescent proteins were also isolated from *Physalia* species and their N-terminal amino acid sequences were determined (WO 03/017937).

cDNA encoding *A. victoria* GFP was cloned by Prasher et al. (Gene (1992), 111(2):229-33). It turned out, that this gene can be heterologically expressed in practically any organism due to unique ability of GFP to form fluorophore by itself (Chalfie et al., Gene (1992), 111(2):229-233). This finding opens broad perspectives for use of GFP in cell biology as a genetically encoded fluorescent label.

The GFP was applied for wide range of applications including the study of gene expression and protein localization (Chalfie et al., Science 263 (1994), 802-805, and Heim et al. in Proc. Nat. Acad. Sci. (1994), 91: 12501-12504), as a tool for visualizing subcellular organelles in cells (Rizzuto et al., Curr. Biology (1995), 5: 635-642), for the visualization of protein transport along the secretory pathway (Kaether and Gerdes, FEBS Letters (1995), 369: 267-271).

A great deal of research is being performed to improve the properties of GFP and to produce GFP reagents useful and optimized for a variety of research purposes. New versions of GFP have been developed, such as a "humanized" GFP DNA, the protein product of which has increased synthesis in mammalian cells (Haas, et al., Current Biology (1996), 6: 315-324; Yang, et al., Nucleic Acids Research (1996), 24: 4592-4593). One such humanized protein is "enhanced green fluorescent protein" (EGFP). Other mutations to GFP have resulted in blue-, cyan- and yellow-green light emitting versions. Despite the great utility of GFP, however, other fluorescent proteins with properties similar to or different from GFP would be useful in the art. In particular, benefits of novel fluorescent proteins include fluorescence resonance energy transfer (FRET) possibilities based on new spectra and better suitability for larger excitation. In 1999 GFP homologs were cloned from non-bioluminescent *Anthozoa* species (Matz et al., Nature Biotechnol. (1999), 17: 969-973). This discovery demonstrated that these proteins are not necessary component of bioluminescence machinery. *Anthozoa*-derived GFP-like proteins showed great spectral diversity including cyan, green, yellow, red fluorescent proteins and purple-blue non-fluorescent chromoproteins (CPs) (Matz et al., Bioessays (2002), 24(10):953-959).

The major drawback of the *Anthozoa*-derived GFP-like is strong oligomerization that hampers the use of these proteins in many applications (Lauf et al., FEBS Lett. (2001), 498: 11-15; Campbell et al., Proc. Natl. Acad. Sci. USA (2002), 99: 7877-7882; Mizuno et al., Biochemistry (2001), 40: 2502-2510). Accordingly, it is an object to provide novel monomeric fluorescent proteins of different colors as well as DNAs encoding them that do not suffer from the drawbacks of the known GFP.

*Hydrozoa* species are potential source of such proteins. Except *Aequorea victoria* GFP and GFP homologues from other *Aequorea* species, like very close GFP homologues from *Aequorea macrodactyla* (GenBank accession numbers AF435427-AF435433) and *Aequorea coerulescens* (Gurskaya et al., Biochem J. (2003), 373(Pt 2): 403-408), no other genes encoding fluorescent proteins from *Hydrozoa* are cloned to date although some of them were characterized at protein level very long ago. Cloning and mutagenesis of the non-*Aequorea Hydrozoa* fluorescent proteins is a perspective way to obtain novel fluorescent labels with improved features.

SUMMARY OF THE INVENTION

The present invention provides nucleic acid molecules encoding novel fluorescent or chromo-proteins and mutants, and derivatives thereof. Said nucleic acid may be isolated, synthesized or present in its non-natural environment.

In certain embodiments, the nucleic acid of the present invention is isolated from non-*Aequorea Hydrozoa* species including *Phialidium* sp., and two fluorescent jellyfishes or hydroid medusae 1 and 2 (hydromedusae 1 and 2) of suborder Anthomedusae, or mutants or derivatives thereof.

In certain embodiments, the nucleic acid of the present invention encodes a protein that has an amino acid sequence, selected from the group consisting of SEQ ID NOs: 2, 4, 6, 8, 10, 12, 14, 16, 18, 20, or 22. In certain embodiments, the nucleic acid encodes a homologue, mutant, derivative, mimetic or a fragment of said protein.

In certain embodiments, the nucleic acid of the present invention has a nucleotide sequence selected from the group consisting of SEQ ID NOs: 1, 3, 5, 7, 9, 11, 13, 15, 17, 19 or 21 or that is homologous, substantially the same, or identical thereto. Nucleic acid sequences that differ from the nucleic acid sequences of the present due to the degeneracy of genetic code or hybridize thereto, are also within the scope of the present invention.

In another embodiments, the invention is directed to proteins that are encoded by the subject nucleic acids, or substantially similar thereto, or homologues, derivatives, or mutants thereof, or is directed to fusion proteins comprising the proteins of the present invention.

Fragments of the nucleic acids of the present invention and nucleic acids that hybridize under high stringency conditions to the nucleic acids of the present invention are also provided.

In yet other embodiments there are provided vectors comprising a nucleic acid of the present invention. In addition, the present invention provides expression cassettes comprising a nucleic acid of the present invention and regulatory elements necessary for expression of the nucleic acid in the cell.

In yet another embodiment, there are provided methods of producing a chromogenic and/or fluorescent protein comprising expressing of a protein in a suitable host-cell and isolating the protein therefrom. Said method comprises (a) providing a nucleic acid molecule of present invention encoding fluorescent or chromo-protein coupling with suitable expression regulation sequences, (b) expressing the protein from said nucleic acid molecule, and (c) isolating the protein substantially free from other proteins.

In addition, antibodies specific for the proteins or fragments thereof of the present invention are provided.

Additionally, host-cells, stable cell lines, transgenic animals and transgenic plants comprising nucleic acids, vectors or expression cassettes of the present invention are provided.

In yet another embodiment, oligonucleotides or probes comprising the nucleotide sequences capable of hybridizing to the subject nucleic acids are provided.

Also provided are methods that use a chromo- or fluorescent protein of the present invention or the nucleic acid encoding it.

In preferred embodiment the method for labeling a biological molecule is provided, said method comprising coupling said biological molecule to the protein of the present invention.

In another preferred embodiment the method for labeling a cell is provided, said method comprising production of the protein of the present invention in the cell.

In another preferred embodiment the method for labeling a cell organelle is provided, said method comprising production of the protein of the present invention fused to a suitable subcellular localization signal in the cell.

In yet another preferred embodiment the method for analyzing a biological molecule, cell or cell organelle is provided, said method comprising detection of a fluorescence signal from protein of the present invention.

In yet another preferred embodiment the method for analyzing a biological molecule, cell or cell organelle is provided, said method comprising expression of a nucleic acid molecule of the present invention in a cell.

Additionally, kits comprising nucleic acids or vectors or expression cassettes harboring said nucleic acids, or protein of the present invention are provided.

BRIEF DESCRIPTION OF THE FIGURES

FIG. 1 shows the alignment of GFP (SEQ ID NO:23), phiYFP (SEQ ID NO:2), hydr1GFP (SEQ ID NO:12) and hm2CP (SEQ ID NO:14) amino acid sequences. Introduced gaps are shown by dots. Residues identical to the corresponding amino acids in GFP are represented by dashes.

FIG. 3 illustrates the excitation-emission spectra for phiYFP-M1G1 (A) and phiYFP-M1C1 (B) proteins.

FIG. 4 represents sketches of the hydromedusa 1 (A) and hydromedusa 2 (B) of sub-order Anthomedusae.

DETAILED DESCRIPTION OF THE INVENTION

Figure 2A:
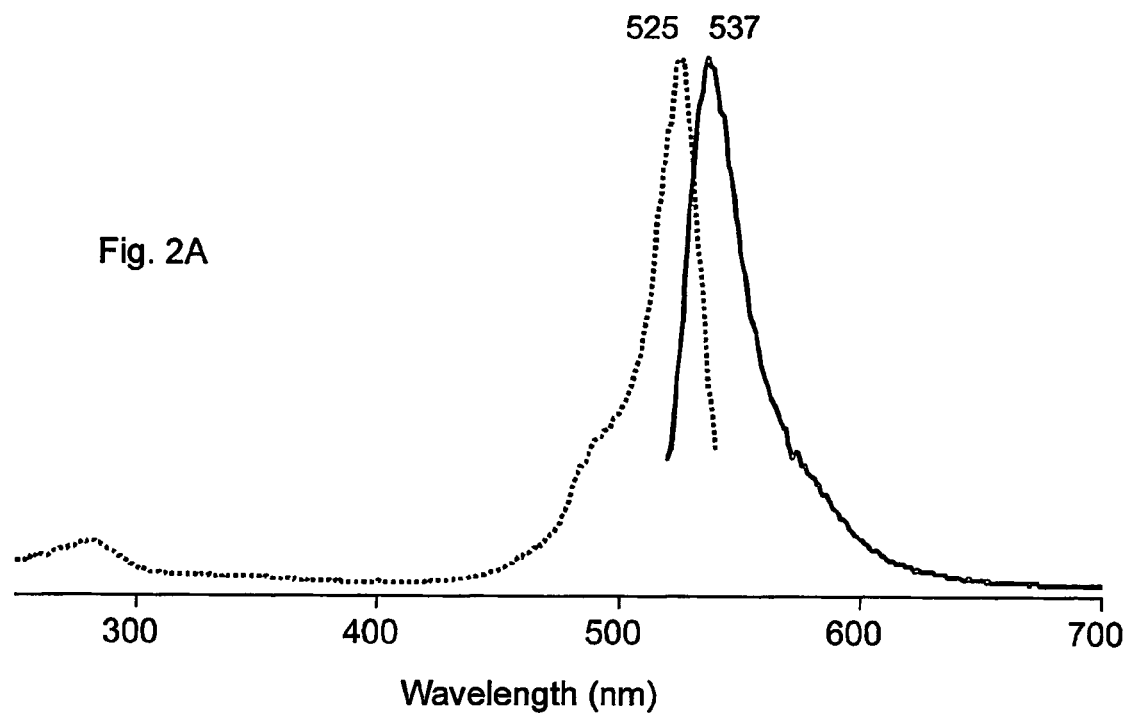
FIG. 2 illustrates the excitation (dashed line) and emission (solid line) spectra for wild type phiYFP (A) and mutants thereof: phiYFP-Y1 (B), phiYFP-M0 (C), and phiYFP-M1 (D).

As used herein the term "fluorescent protein" or "fluoroprotein" means a protein that is fluorescent; e.g., it may exhibit low, medium or intense fluorescence upon irradiation with light of the appropriate excitation wavelength. The fluorescent characteristic of these proteins is one that arises from the interaction of two or more amino acid residues of the protein, and not from a single amino acid residue. As such, the fluorescent proteins of the present invention do not include proteins that exhibit fluorescence only from residues that act by themselves as intrinsic fluors, i.e., tryptophan, tyrosine and phenylalanine.

As used herein the term "chromoprotein" or "chromogenic protein" means a colored protein, which may be fluorescent, low or non-fluorescent. As used herein, the terms "chromoprotein" and "fluorescent protein" do not include luciferases, such as Renilla luciferase.

As used herein, the term "GFP" refers to the green fluorescent protein from *Aequorea victoria*, including prior art versions of GFP engineered to provide greater fluorescence or fluoresce in different colors. The sequence of wild type GFP has been disclosed in Prasher et al., Gene 111 (1992), 229-33.

As used herein, the term "EGFP" refers to mutant variant of GFP having two amino acid substitutions: F64L and S65T (Heim et al., Nature 373 (1995), 663-664).

As used herein the term "isolated" means a molecule or a cell that is an environment different from that in which the molecule or the cell naturally occurs.

As used herein the term "fragment" is meant to comprise e.g. an alternatively spliced, or truncated, or otherwise cleaved nucleic acid molecule or protein.

As used herein the term "derivative" refers to a mutant, or an RNA-edited, or a chemically modified, or otherwise altered nucleic acid molecule, or to a mutant, or chemically modified, or otherwise altered protein.

As used herein the term "mutant" refers to protein disclosed in the present invention, in which one or more amino acids are added and/or substituted and/or deleted and/or inserted at the N-terminus, and/or the C-terminus, and/or within the native amino acid sequences of the proteins of the present invention. As used herein the term "mutant" refers to nucleic acid molecule that encode a mutant protein. Moreover, the term "mutant" refers to any shorter or longer version of the protein or nucleic acid herein.

As used herein, "homologue or homology" is a term used in the art to describe the relatedness of a nucleotide or peptide sequence to another nucleotide or peptide sequence, which is determined by the degree of identity and/or similarity between said sequences compared.

As summarized above the present invention is directed to nucleic acid molecules encoding a fluorescent and chromoproteins and mutants, variants and derivatives thereof, as well as proteins and peptides encoded by these nucleic acids. The nucleic acid molecules and proteins of interest are isolated from non-*Aequorea Hydrozoa* species. The proteins of interest include yellow fluorescent protein, phiYFP, from *Phialidium* sp., green fluorescent protein hydr1GFP from hydroid medusa 1 (hydromedusa 1) of sub-order Anthomedusae, and purple chromoprotein, hm2CP from hydroid medusa 2 (hydromedusa 2) of sub-order Anthomedusae. Also of interest are proteins that are substantially similar to, or derivatives, or homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided. The subject protein and nucleic acid compositions find use in a variety of different applications and methods, particularly protein labeling applications. Finally, kits for use in such methods and applications are provided.

Nucleic Acid Molecules

The present invention provides nucleic acid molecules encoding fluorescent/chromo-proteins from *Hydrozoa* species, other than from *Aequorea* genus, derivatives, mutants, and homologues of these proteins, as well as fragments thereof. A nucleic acid molecule as used herein is DNA molecules, such as genomic DNA molecules or cDNA molecules, or RNA molecules, such as mRNA molecules. In particular, said nucleic acid molecules is cDNA molecules having an open reading frame that encodes a *Hydrozoa* chromo/fluorescent protein of the invention or fragment thereof and is capable, under appropriate conditions, of being expressed as a fluorescent/chromo-protein or protein fragment (peptide) according to the invention. The invention also encompasses nucleic acids that are homologous, substantially similar to, identical to, derived from, or mimetics of the nucleic acids encoding proteins or protein fragments of the present invention. The subject nucleic acids are present in an environment other than their natural environment; e.g., they are isolated, present in enriched amounts, or are present or expressed in vitro or in a cell or organism other than their naturally occurring environment.

Specific nucleic acid molecules of interest are those that encode following *Hydrozoa* chromo/fluoroproteins (and homologs/derivates/mutants thereof): yellow fluorescent protein, phiYFP from *Phialidium* sp., green fluorescent protein, hydr1GFP from hydroid medusa 1 of sub-order Anthomedusae, and purple chromoprotein, hm2CP from hydroid medusa 2 of sub-order Anthomedusae. Each of these particular types of nucleic acid molecules of interest is now discussed in greater detail individually.

phiYFP

The nucleic acid molecules encoding fluorescent/chromo-proteins may be isolated from an organism from class Hydrozoa, preferably from Order Hydroida, more preferably from Sub-order Leptomedusae, more preferably from Family Campanulariidae, and even more preferably from Genus *Phialidium*. In the particularly preferred embodiment the nucleic acid molecule isolated from *Phialidium* sp., encodes a specific protein named PhiYFP. Homologues/mutants/derivates of this protein such as phiYFP-Y1, phiYFP-M1, phiYFP-M0, phiYFP-M1G1 (i.e. phiYFP-G1 or phiGFP1), and phiYFP-M1C1 (i.e. phiYFP-C1 or phiCFP1), described below in more details in the experimental part are also of particular interest. The deduced wild type cDNA coding sequence for PhiYFP is depicted in SEQ ID NO: 01.

hydr1GFP

The nucleic acid molecules encoding fluorescent/chromo-proteins may be isolated from an organism from class Hydrozoa, preferably from Order Hydroida, more preferably from Sub-order Anthomedusae. The specific protein encoded by such nucleic acid molecule is named hydr1GFP (i.e. anm1GFP1). Homologues/mutants/derivates of this protein are also of particular interest. The deduced wild type cDNA coding sequence for hydr1GFP is depicted in SEQ ID No: 11.

hm2CP

The nucleic acid molecules encoding fluorescent/chromo-proteins may be isolated from an organism from class Hydrozoa, preferably from Order Hydroida, more preferably from Sub-order Anthomedusae. The specific protein encoded by such nucleic acid molecule is named hm2CP (i.e. anm2CP). Homologues/mutants of this protein such as S3-2 red fluorescent mutant of hm2CP, described below in more details in the experimental part are also of particular interest. The deduced wild type cDNA coding sequence for hm2CP is depicted in SEQ ID No: 13.

Homologs of the above-described nucleic acid molecules are also of interest. The source of homologous nucleic acids may be any species of plant or animal or the sequence may be wholly or partially synthetic including nucleic acid mimetics. In certain embodiments, the nucleic acid of the present invention has a sequence similarity with corresponding homologs on the nucleotide or amino acid levels of at least about 40%, and, preferably about 50%, 55%, 60%, 65%, 70%, or higher, including 75%, 80%, 85%, 90% and 95% or higher. A reference sequence will usually be at least about 60 nucleotides long, more usually at least about 80 nucleotides long, and may extend to the complete sequence that is being compared. Sequence similarity is calculated based on a reference sequence. Algorithms for sequence analysis are known in the art, such as BLAST, described in Altschul et al., J. Mol. Biol., 215, pp. 403-10 (1990) (for example, using default settings, i.e., parameters w=4 and T=17).

Homologs are identified by any of a number of methods. A fragment of a cDNA of the present invention may be used as a hybridization probe against a cDNA library from a target organism using low stringency conditions. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) followed by washing at 55° C. in 1×SSC (01.15 M sodium chloride/0.015 M sodium citrate). Sequence identity may be determined by hybridization under high stringency conditions, for example, at 50° C. or higher and 0.1×SSC (15 mM sodium chloride/1.5 mM sodium citrate). Nucleic acids having a region of substantial identity to the provided sequences, e.g., allelic variants, genetically-altered versions of the nucleic acid, etc., bind to the provided sequences under high stringency hybridization conditions. By using probes, particularly labeled probes of DNA sequences, one can isolate homologous or related genes.

Also provided are nucleic acids that hybridize to the above-described nucleic acids under stringent conditions, preferably under high stringency conditions (i.e., complements of the previously-described nucleic acids). An example of stringent conditions is hybridization at 50° C. or higher and 0.1×SSC (15 mM sodium chloride/1.5 mM sodium citrate). Another example of high stringency hybridization conditions is overnight incubation at 42° C. in a solution of 50% formamide, 5×SSC (150 mM NaCl, 15 mM trisodium citrate), 50 mM sodium phosphate (pH7.6), 5×Denhardt's solution, 10% destran sulfate, and 20 μg/ml denatured, sheared salmon sperm DNA, followed by washing in 0.1×SSC at about 65° C.

Other high stringency hybridization conditions are known in the art and may also be used to identify nucleic acids of the invention.

Nucleic acids encoding variants, mutants or derivatives of the proteins of the invention also are provided. Mutants or derivates can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof. In some embodiments, fluorescent proteins encoded by mutant or derived nucleic acids have the same fluorescent properties as the wild type fluorescent protein. In other embodiments, mutant or derived nucleic acids encode fluorescent proteins with altered spectral properties, as described in more detail for mutants phiYFP-Y1, phiYFP-M1, phiYFP-M1G1, phiYFP-M1C1, S3-2 herein.

In addition, degenerated variants of the nucleic acids that encode the proteins of the present invention are also provided. Degenerated variants of nucleic acids comprise replacements of the codons of the nucleic acid to the another codons encoding the same amino acids. In particular, degenerated variants of the nucleic acids is generated to increase its expression in a host cell. In this embodiment, codons of the nucleic acid that are non-preferred or a less preferred in genes in the host cell are replaced with the codons over-represented in coding sequences in genes in the host cell, wherein said replaced codons encodes the same amino acid. Humanized versions of the nucleic acids of the present invention are under particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins, the disclosure of which is herein incorporated by reference.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' un-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids up to the full length protein.

The subject nucleic acids may be isolated and obtained in substantially purified form. Substantially purified form means that the nucleic acids are at least about 50% pure, usually at least about 90% pure and are typically "recombinant", i.e., flanked by one ore more nucleotides with which it is not normally associated on a naturally-occurring chromosome in its natural host organism.

The nucleic acids of the present invention, e.g. having the sequence of SEQ ID NOs: 01, 03, 05, 07, 09, 11, 13, 15, 17, 19 or 21, the corresponding cDNAs, full-length genes and constructs can be generated synthetically by a number of different protocols known to those of skill in the art. Appropriate nucleic acid constructs are purified using standard recombinant DNA techniques as described in, for example, Sambrook et al., Molecular Cloning: A Laboratory Manual, $2^{nd}$ Ed., (1989) Cold Spring Harbor Press, Cold Spring Harbor, N.Y., and under regulations described in, e.g., United States Dept. of HHS, National Institute of Health (NIH) Guidelines for Recombinant DNA Research.

Also provided are nucleic acids that encode fusion proteins comprising a protein of the present invention, or fragments thereof that are discussed in more details below.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or fill-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject chromogenic or fluorescent proteins or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operably linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g. the co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus* oocytes, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also of interest are promoter sequences of the genomic sequences of the present invention, where the sequence of the 5' flanking region may be utilized for promoter elements, including enhancer binding sites, that, for example, provide for regulation of expression in cells/tissues where the subject proteins gene are expressed.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

The subject nucleic acids, including flanking promoter regions and coding regions, may be mutated in various ways known in the art to generate targeted changes in promoter strength or to vary the sequence of the encoded protein or properties of the encoded protein, including the fluorescent properties of the encoded protein.

In many embodiments, nucleic acids found in *Aequorea* species are not included within the scope of the invention. In certain embodiments, the GFP homolog and nucleic acids encoding the same from are *Aequorea victoria, Aequorea macrodactyla*, and *Aequorea coerulscens* not included within the scope of the subject invention.

Proteins

Also provided by the subject invention are non-*Aequorea Hydrozoa* chromo- and fluorescent proteins and mutants thereof including full-length proteins, as well as portions or fragments thereof. Also provided variations of the naturally occurring protein, where such variations are homologous or substantially similar to the naturally occurring protein, and mutants of the naturally occurring proteins, as described in greater detail below.

In many embodiments, the subject proteins have an absorbance maximum ranging from about 300 to 700, usually from about 350 to 650 and more usually from about 400 to 600 nm. Where the subject proteins are fluorescent proteins, by which is meant that they can be excited at one wavelength of light following which they will emit light at another wavelength, the excitation spectra of the subject proteins typically ranges from about 300 to 700 nm. The subject proteins generally have a maximum extinction coefficient that ranges from about 25,000 to 150,000 and usually from about 45,000 to 129,000. The subject proteins typically range in length from about 150 to 300 amino acids and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the chromo- and fluorescent proteins can be detected by common methods (e. g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest are chromo/fluoroproteins (and homologs, mutants, and derivates thereof) from the non-*Aequorea Hydrozoa* species: phiYFP from *Phialidium* sp., green fluorescent protein, hydr1GFP from hydroid medusa 1 (hydromedusa 1) of sub-order Anthomedusae, and purple chromoprotein, hm2CP from hydroid medusa 2 (hydromedusa 2) of sub-order Anthomedusae. Each of these particular types of polypeptide compositions of interest is now discussed in greater detail individually.

phiYFP (and Derivates/Mutants Thereof)

The proteins of this embodiment have an absorbance maximum ranging from about 350 to 550, usually from about 450 to 550 and often from about 435 to 540 nm, e.g., 515 to 530 nm or 480 to 490, while the emission maximum typically ranges from about 400 nm to 650 nm and more usually from about 450 to 600 nm while in many embodiments the emission spectra ranges from about 470 to 550 nm, e.g., 505 to 515 or 520 to 530 nm, or 530 to 540 nm. The subject proteins typically range in length from about 200 to 250, usually from about 210 to 240 amino acid residues, and generally have a molecular weight ranging from about 20 to 30, usually from about 22.50 to 27.50 kDa. Of particular interest in many embodiments is phiYFP, which has an amino acid sequence as shown in SEQ ID NO: 02. Also of interest are mutants and derivates of this sequence, e. g., phiYFP-Y1, phiYFP-M1, phiYFP-M0, phiYFP-M1G1 and phiYFP-M1C1, as in SEQ ID NOs: 04, 06, 08, 18 and 20, respectively.

hydr1GFP (and Derivates/Mutants Thereof)

In many embodiments, the subject proteins have an absorbance maximum ranging from about 400 to 600 and more usually from about 450 to 550 nm, and often from about 460 to 500 nm, e.g., 470 to 480 nm, while the emission spectra of the subject proteins typically ranges from about 450 to 650, usually from about 460 to 600 nm and more usually from about 480 to 550 nm, e.g., 480 to 500 nm, and sometimes 490 to 500 nm. The subject proteins typically range in length from about 200 to 300 amino acids and usually from about 220 to 290 amino acid residues, and generally have a molecular weight ranging from about 25 to 35 kDa, usually from about 26.5 to 32.5 kDa. Of particular interest in many embodiments is wild type hydr1GFP fluorescent protein, which has an amino acid sequence as shown in SEQ ID NO: 12, mutants and derivatives thereof.

hm2CP (and Mutants Thereof)

In many embodiments, the subject proteins have an absorbance maximum ranging from about 350 to 650, usually from about 450 to 600 and more usually from about 490 to 595 nm, e.g., 560 to 590 nm, while the emission spectra of the subject proteins typically ranges from about 450 to 650, usually from about 500 to 640 nm and more usually from about 580 to 620 nm, e.g., 590 to 620 nm. The subject proteins typically range in length from about 200 to 250, usually from about 210 to 240 amino acid residues, and generally have a molecular weight ranging from about 20 to 30 kDa, usually from about 22.50 to 27.50 kDa. Of particular interest in many embodiments is hm2CP (anm2CP), which has an amino acid sequence as shown in SEQ ID NO: 14. Also of interest are mutants of this sequence, e. g., red fluorescent protein S3-2, and the like, as provided, for example, in SEQ ID NO: 16.

Homologs or proteins that vary in sequence from the above provided specific amino acid sequences of the subject invention, i. e., SEQ ID NOs: 02, 04, 06, 08, 10, 12, 14, 16, 18, 20 or 22, are also provided. By homolog is meant a protein having at least about a protein having at least about 55%, usually at least about 60% and more usually at least about 65% amino acid sequence identity to amino acid sequences SEQ ID NOS 02, 04, 06, 08, 10, 12, 14, 16, 18, 20 or 22 as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5). In many embodiments, homologs of interest have much higher sequence identity e.g., 70%, 75%, 80%, 85%, 90% (e.g., 92%, 93%, 94%) or higher, e.g., 95%, 96%, 97%, 98%, 99%, 99.5%, particularly for the sequence of the amino acids that provide the functional regions of the protein.

Also provided are proteins that are substantially identical to the wild type protein, where by substantially identical is meant that the protein has an amino acid sequence identity to the sequence of wild type protein of at least about 60%, usually at least about 65% and more usually at least about 70%, where in some instances the identity may be much higher, e. g., 75%, 80%, 85%, 90%, 95% or higher.

Proteins that are derivatives or mutants of the above-described naturally occurring proteins are also provided. Mutants and derivatives may retain biological properties of the wild type (e.g., naturally occurring) proteins, or may have biological properties which differ from the wild type proteins. The term "biological property" of the proteins of the present invention refers to, but is not limited to, spectral properties, such as absorbance maximum, emission maximum, maximum extinction coefficient, brightness (e.g., as compared to the wild type protein or another reference protein such as green fluorescent protein (GFP) from *A. victoria*), and the like; biochemical properties, such as in vivo and/or in vitro stability (e.g., half-life); maturation speed, aggregation tendency and oligomerization tendency and other such properties. Mutations include single amino acid changes, deletions or insertions of one or more amino acids, N-terminal truncations or extensions, C-terminal truncations or extensions and the like.

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g. biochemical, spectral, etc.) property has been altered. For example, fluorescence intensity can be measured using a spectrophotometer at various excitation wavelengths.

Derivatives can be also generated using standard techniques and includes RNA-editing, chemical modifications, posttranslational and posttranscriptiolnal modifications and the like. For instance, derivatives can be generated by processes such as altered phosphorylation, or glycosylation, or acetylation, or lipidation, or by different types of maturation cleavage and the like.

Those proteins of the subject invention that are naturally-occurring proteins are present in a non-naturally occurring environment, e.g., are separated from their naturally-occurring environment. For example, purified protein is provided, where "purified" means that the protein is present in a mixture that is substantially free of non-chromogenic or fluorescent proteins of interest, where "substantially free" means that less than 90%, usually less than 60% and more usually less than 50% of the mixture content is non-chromogenic or fluorescent proteins or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially purified form, where by "substantially purified form" means at least 95%, usually at least 97% and more usually at least 99% pure.

Fragments of the naturally-occurring proteins as well as of the mutant and derivate proteins described above are also provided. Biologically active fragments and/or fragments corresponding to functional domains, and the like are in a particular interest. Fragments of interest are polypeptides that are typically at least about 30 amino acids in length, usually at least about 50 amino acids in length, preferably of at least about 75 or 100 amino acids in length and may be as long as 300 amino acids in length or longer, but will usually not exceed about 250 amino acids in length, where the fragment will have a stretch of amino acids that is identical to the subject protein of at least about 25 amino acids, and usually at least about 45 amino acids, and in many embodiments at least about 50 amino acids in length. In some embodiments, the subject polypeptides are about 25 amino acids, about 50, about 75, about 100, about 125, about 150, about 200, or about 250 amino acids in length, up to the entire length of the protein. In some embodiments, a protein fragment retains all or substantially all of the specific property of the wild type protein.

The subject proteins and polypeptides may be obtained from naturally occurring sources or synthetically produced. For example, wild type proteins may be derived from biological sources which express the proteins, e. g., *Hydrozoa* species, such as the specific ones listed above. The subject proteins may also be derived from synthetic means, e. g. by expressing a recombinant nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may be prepared from the original source and purified using HPLC, exclusion chromatography, gel electrophoresis, affinity chromatography, and the like.

Also provided fusion proteins comprising a protein of the present invention, or fragments thereof, fused, for example, to a degradation sequence, a sequence of subcellular localization (e.g. nuclear localization signal, peroximal targeting signal, Golgi apparatus targeting sequence, mitochondrial targeting sequence, etc.), a signal peptide, or any protein or polypeptide of interest. Fusion proteins may comprise for example, a fluoro/chromo-protein of subject invention polypeptide and a second polypeptide ("the fusion partner") fused in-frame at the N-terminus and/or C-terminus of the fluoro/chromo polypeptide. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the fluoro/chromo-protein portion of the fusion protein, and is typically not a *Hydrozoa* fluoro/chromo-proteins of subject invention orderivative/fragment thereof; i.e., it is not found in *Hydrozoa* species.

Also provided are antibodies that bind specifically to the fluorescent or chromo-proteins of the present invention. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, F(ab')$_2$ and Fab are also of interest.

Transgenics

The nucleic acids of the present invention can be used to generate transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g. *Escherichia coli, Streptomyces* sp., *Bacillus subtilis, Lactobacillus acidophilus*, etc) or eukaryotic host-cells. Transgenic organism of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e. DNA) into such organisms are widely known and provided in references such as Sambrook et al. (Molecular Cloning: A Laboratory Manual, $3^{rd}$ Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example yeast. Yeast is widely used as a vehicle for heterologous gene expression (for example see Goodey et al Yeast biotechnology, D R Berry et al, eds, (1987) Allen and Unwin, London, pp 401-429) and by King et al Molecular and Cell Biology of Yeasts, E F Walton and G T Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2203) San Diego: Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, where the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Tansformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology (eds. Lea and Leegood, John Wiley & Sons) (1993) pp. 275-295 and in Plant Biotechnology and Transgenic Plants (eds. Oksman-Caldentey and Barz), (2002) 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or Agrobacterium-mediated transformation available for those skilled in the art.

Methods of Use

The fluorescent proteins of the present invention (as well as other components of the subject invention described above) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In a preferred embodiment relating to the method for labeling a biological molecule, cell or cell organelle, the subject proteins find use as in vivo labels (or reporter molecules) in cell and molecular biology assays. The assays of interest include but not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as a biomolecule labels, or cell organelle labels in living and fixed cells; as a markers in cell or organelle fusion, as a cell or organelle integrity markers, as a transfection markers (e.g. as labels for selection of transfected cells containing an expression vector encoding at least one fluorescent protein of the invention), as real-time probe working at near physiological concentrations, etc.

Furthermore, the subject proteins may be used in the method for analyzing a biological molecule. For example, they find use for identifying and/or measuring the expression of protein or polypeptide of interest in biological material. This method comprises: i) introducing into a cell a nucleic acid molecule comprising a nucleotide sequence encoding a fluorescent protein according to the present invention wherein said nucleic acid molecule is operably linked to and under the control of an expression control sequence which moderates expression of said protein or polypeptide of interest; ii) expression of the said nucleic acid under suitable condition; and iii) detecting the fluorescence emission of the fluorescent protein as a means of measuring the expression of the protein of interest.

In particular, the subject proteins find use for identifying and/or measuring the expression and/or localization of protein or polypeptide of interest in biological material. This method comprises: i) introducing into a cell a nucleic acid molecule comprising a nucleotide sequence encoding a fluorescent protein according to the present invention wherein said nucleic acid molecule is fused with sequence encoding protein or polypeptide of interest and operably linked to and under the control of an expression control sequence which moderates expression of said protein or polypeptide of interest; ii) culturing the cell under conditions suitable for the expression of the protein of interest; and iii) detecting the fluorescence emission of the fluorescent protein as a means of measuring the expression/localization of the protein of interest.

The applications of interest include the use of the subject proteins in fluorescence resonance energy transfer (FRET) methods. In these methods, the subject proteins serve as donor and/or acceptors in combination with a second fluorescent protein or dye, for example, an another fluorescent protein of subject invention, or a fluorescent protein as described in Matz et al., Nature Biotechnology 17:969-973 (1999); a green fluorescent protein from Aequorea victoria or fluorescent mutant thereof, for example, as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has $Ca^{2+}$ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins find also use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the fluorescent protein by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescent activity, because parts of the functional chromophore are divided by the spacer. The spacer is framed by two identical protease-specific cleavage sites. Upon cleavage via the activated protease, the spacer would be cut out and the two residual "subunits" of the fluorescent protein would be able to reassemble to generate a functional fluorescent protein. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins. For example, the PH domain of GRP1 has a high affinity to phosphatidyl-inositol tri-phosphate (PIP3) but not to PIP2. As such, a fusion protein between the PH domain of GRP1 and the subject proteins can be constructed to specifically label PIP3-rich areas in biological membranes.

The subject fluorescent proteins also find use as biosensors in prokaryotic and eukaryotic cells, such as a $Ca^{2+}$ ion indicator; a pH indicator; a phosphorylation indicator; or as an indicator of other ions, such as magnesium, sodium, potassium, chloride and halides. Methods of using fluorescent proteins as biosensors also include those described in U.S. Pat. Nos. 5,972,638; 5,824,485 and 5,650,135 (as well as the references cited therein) the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. In preferred embodiments kits may be used for labeling a biological molecule. Kits typically include the protein of the invention as such, or a nucleic acid encoding the same preferably with the elements for expressing the subject proteins, for example, a construct such as a vector comprising a nucleic acid encoding the subject protein. The invention also encompasses means for producing such kit components. Said means may include the cDNA from Hydrozoa medusa and pair of oligonucleotide primers to produce nucleic acid of subject invention, e.g. by PCR, or said means may include a number of the nucleic acid fragments, that when ligated can produce the nucleic acid encoding fluorescent protein of the present invention, etc. The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following example is offered by way of illustration and not by way of limitation.

EXAMPLES

Example 1 phiYFP Cloning, Sequencing and Recombinant Protein Production

Bright yellow fluorescence was detected using a fluorescent microscope in Hydromedusa *Phialidium* sp. (*Cnidaria; Hydrozoa; Hydroida; Leptomedusae; Campanulariidae*). To find the protein responsible for fluorescence in this jellyfish, a strategy based on the screening of an expression cDNA library in *E. coli* was chosen. Amplified cDNA samples were prepared using a SMART cDNA amplification kit (Clontech) and cloned into PCR-Script vector (Stratagene). About $10^5$ recombinant clones were screened visually using a fluorescent stereomicroscope. Two fluorescent clones encoding the same yellow fluorescent proteins were found and were named phiYFP. The nucleic acid and amino acid sequences for phiYFP are shown in SEQ NOs: 01, 02 and 23. Comparison of phiYFP with *A. victoria* GFP is shown in FIG. 1. phiYFP appears to be more similar to GFP (50% identity) than to coral-derived fluorescent proteins.

To facilitate protein purification, the coding region of the phiYFP gene was cloned into a pQE30 expressing vector (Qiagen), so that recombinant protein contained a six-histidine tag at its N-terminus. After expression in *E. coli*, phiYFP protein was purified via a metal-affinity resin TALON (Clontech). Excitation-emission spectra for phiYFP peaked at 525 nm and 537 nm (FIG. 2A), respectively. In contrast to wild type *A. victoria*, GFP, the novel protein possessed only one absorption-excitation peak, probably corresponding to a deprotonated chromophore state.

Example 2

PhiYFP Mutagenesis

Figure 2B:
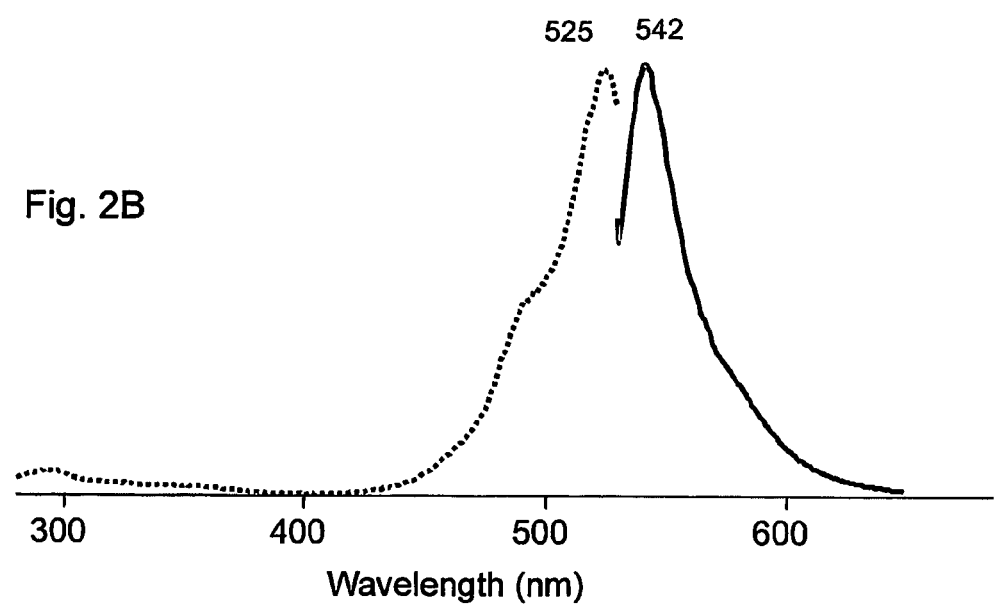

The PhiYFP nucleic acid coding sequence was prepared as described above in the Example 1. We have modified the encoded wild-type protein by random mutagenesis. Random mutagenesis of phiYFP resulted in the generation of a brighter mutant named phiYFP-Y1 with a slightly altered excitation-emission spectra. This mutant contained three amino acid substitutions, specifically S2P, E174G, I201M (SEQ ID NOs: 03, 04, and 24). phiYFP-Y1 exhibited a brightness 1.5 to 2 fold higher than the wild type phiYFP in a side-by-side visual comparison of *E. coli* colonies expressing these fluorescent proteins. In addition, phiYFP-Y1 demonstrates a slightly red-shifted emission spectrum that peaked at 542 nm (see FIG. 2B).

Both phiYFP and phiYFP-Y1 proteins were found to be dimeric. It was demonstrated by protein gel-electrophoresis of non-heated protein samples (see Baird et al., supra, 2000). Under these conditions these FPs migrated as yellow fluorescent band at about 50 kDa. Gel-filtration tests proved dimeric state of phiYFP and phiYFP-Y1. Purified protein samples (~1 mg/ml) were loaded onto a Sephadex-100 column (0.7×60 cm) and eluted with a solution of 50 mM phosphate buffer (pH 7.0) and 100 mM NaCl. EGFP, HcRed1 and DsRed2 (Clontech) were used as monomer, dimer and tetramer standards, respectively.

Site-directed mutagenesis was used to create monomeric variant of phiYFP-Y1. Six amino acid substitutions were introduced, specifically V103N, M166R, Y198N, T202S, T206K, V221K. Totally, this mutant phiYFP-M0 carried 9 substitutions: S2P, V103N, M166R, E174G, Y198N, I201M, T202S, T206K, V221K (SEQ ID NOs: 05, 06, and 25). phiYFP-M0 demonstrated slow protein folding and low brightness when it was expressed in *E. coli*. Its excitation-emission spectra were blue-shifted compared to the parental mutant (maxima at 517 and 529 nm, respectively; FIG. 2C). phiYFP-M0 was monomeric protein in accordance to gel-filtration tests.

To improve phiYFP-M0 we applied random mutagenesis. The Diversity PCR Random Mutagenesis kit (CLONTECH) was used, under conditions optimal for 5-6 mutations per 1000 bp. *E. coli* colonies expressing mutant proteins were visually screened with a fluorescent stereomicroscope SZX-12 (Olympus). The brightest clone with apparently red-shifted spectra (compared to the parental phiYFP-M0) was characterized further. This mutant designated phiYFP-M1 contained the following amino acid substitutions: E88D, V103N, M166C, E174G, I201M, T202S, T206K, V221K (SEQ ID NOs: 07, 08, and 26). Excitation-emission spectra for this protein possessed peaks at 524 and 539 nm, respectively, similarly to that of the wild type phiYFP (FIG. 2D). Purified phiYFP-M1 possessed molar extinction coefficient 130,000 $M^{-1}cm^{-1}$ and fluorescence quantum yield 0.40. For molar extinction coefficient determination, we relied on estimating mature chromophore concentration. Protein was alkali-denatured with an equal volume of 2M NaOH. Under these conditions, the GFP-like chromophore absorbs at 446 nm and its molar extinction coefficient is 44,000 $M^{-1}cm^{-1}$ (Ward, W. W. Properties of the coelentrate green-fluorescent protein in Bioluminescence and Chemiluminescence. Academic Press (1981), 235-242). Absorption spectra for native and alkali-denatured phiYFP-M1 were measured. Molar extinction coefficient for native state protein was estimated based on the absorption of denatured protein. For quantum yield determination, the fluorescence of phiYFP-M1 was compared to equally absorbing EGFP (quantum yield 0.60 (Patterson et al., J. Cell. Sci. (2001), 114: 837-838)). phiYFP-M1 was monomeric protein in accordance to gel-filtration tests.

To enhance expression in mammalian cells we synthesized "humanized" version of phiYFP-M1 using mammalian-optimised codons (SEQ ID NOs: 09, 10, and 27). "Humanized" version of phiYFP-M1 was subjected for site directed and random mutagenesis to obtain green and cyan light emitting versions of the protein. Mutant fluorescent proteins with green and cyan fluorescence were obtained. The green mutant of the humanized phiYFP-M1, named phiYFP-M1G1, contained the following amino acid substitutions (as compared with phiYFP-M1): T65S, L148Q, Y203T, K231T, T232A (SEQ ID NOs: 17, 18, and 31). The cyan mutant of the humanized phiYFP-M1, named phiYFP-M1C1, contained the following amino acid substitutions (as compared with phiYFP-M1): L6Q, T65S, Y66W, N124K, C147Y, L148Q, Y203T, V224L (SEQ ID NOs: 19, 20, and 32). Excitation-emission spectra for this protein are shown at FIGS. 3A,B.

Example 3 hydr1GFP Cloning, Sequencing and Recombinant Protein Production

Bright green fluorescence was detected using a fluorescent microscope in a hydromedusa 1 (about 1 mm in length, FIG. 4) of sub-order Anthomedusae (*Cnidaria, Hydrozoa, Anthomedusae*). To search for the gene responsible for the fluorescence in this jellyfish, a strategy based on screening of an expression cDNA library in *E. coli* was implemented. Amplified cDNA samples were prepared using a SMART cDNA amplification kit (Clontech) and cloned into the PCR-Script vector (Stratagene). About $10^5$ recombinant clones were screened visually using a fluorescent stereomicroscope. Three fluorescent clones were identified, each encoding the same green fluorescent protein, which was named hydr1GFP. The nucleotide and amino acid sequences for this protein are shown in SEQ ID NOS: 11, 12, and 28. A comparison of hydr1GFP with *A. victoria* GFP is shown in FIG. 1. hydr1GFP appears to be more similar to GFP (37% identity) than to fluorescent proteins from corals.

Figure 5:
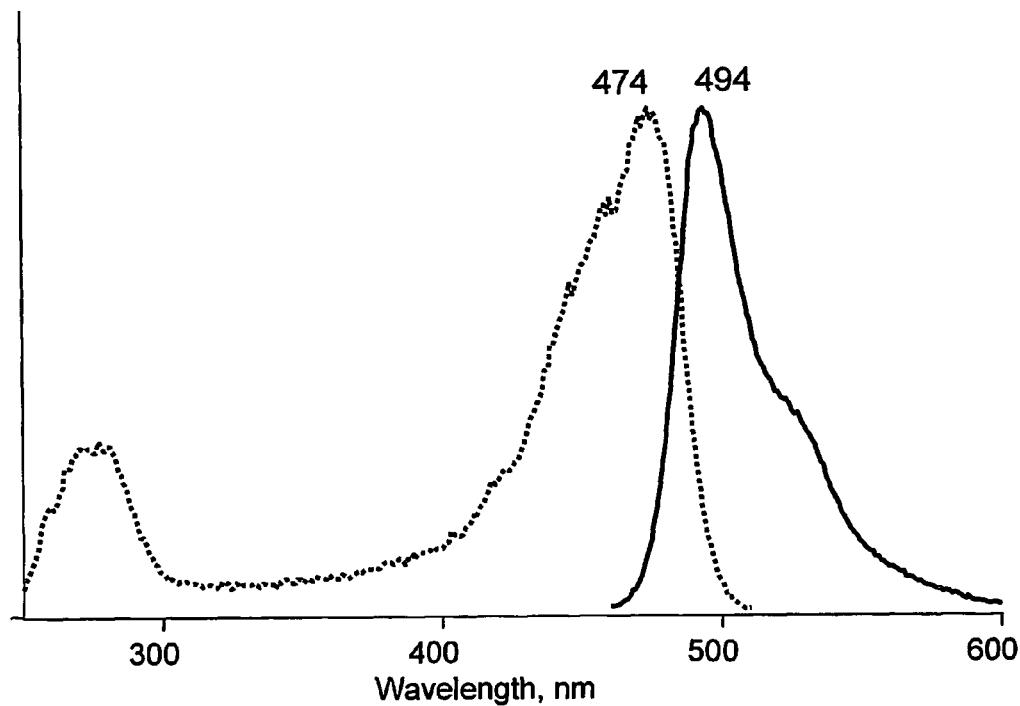
FIG. 5 illustrates the excitation-mission spectra for wild type hydr1GFP.

To facilitate protein purification, the coding region of hydr1GFP was cloned into pQE30 expressing vector (Qiagen), so that recombinant protein contained six-histidine tag at its N-terminus. After expression in *E. coli*, hydr1GFP was purified by the metal-affinity resin, TALON (Clontech). The excitation-emission spectra for hydr1GFP showed peaks at 474 nm and 494 nm (FIG. 5). In contrast to wild type *A. victoria* GFP, the novel hydr1GFP protein possessed only one absorption-excitation peak, which may correspond to a deprotonated chromophore state.

Example 4 hm2CP Cloning, Sequencing and Recombinant Protein Production

Bright green fluorescence was detected in small hydromedusa 2 of sub-order Anthomedusae (*Cnidaria, Hydrozoa, Anthomedusae*) using fluorescent microscope. To search for FP from this jellyfish we chose a strategy based on screening of expression cDNA library in *E. coli*. Amplified cDNA samples were prepared using SMART cDNA amplification kit (Clontech) and cloned into PCR-Script vector (Stratagene). About $10^5$ recombinant clones were visually screened using fluorescent stereomicroscope or naked eyes. Unexpectedly, we did not observed fluorescent clones. Instead, purple non-fluorescent CP (hm2CP) was identified. Nucleotide and amino acid sequences for this protein is shown in SEQ ID NOs: 13, 14 and, 29. Comparison of hm2CP with GFP is shown in FIG. 1. hm2CP appears to be relatively distant GFP homolog (as low as 24% identity).

Figure 6:
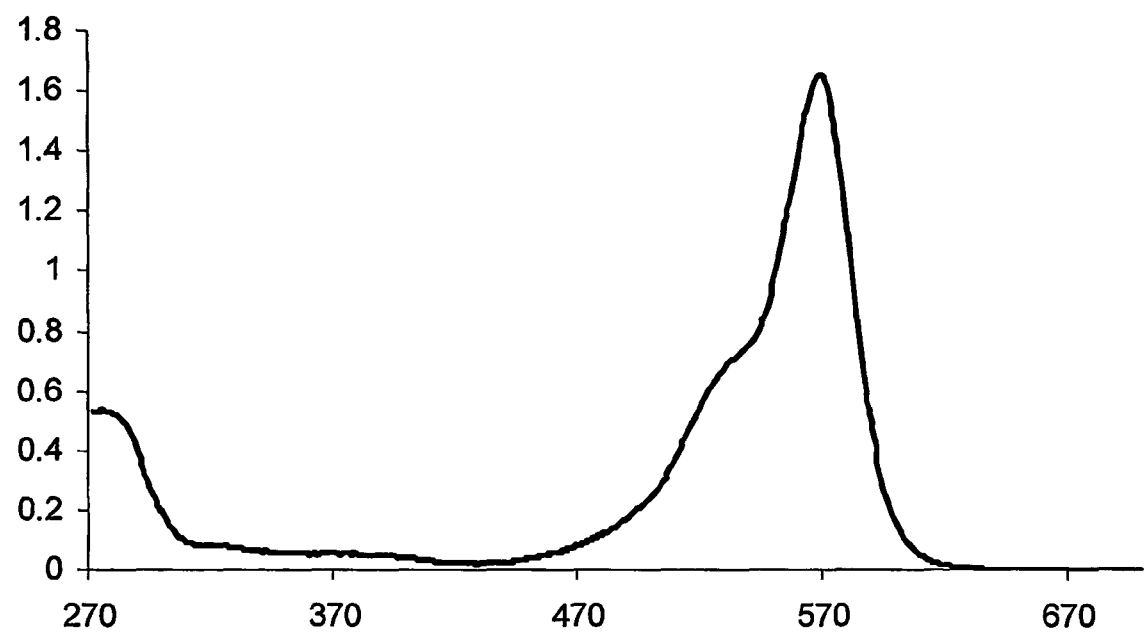
FIG. 6 illustrates the absorption spectrum for wild type hm2CP.
Figure 7:
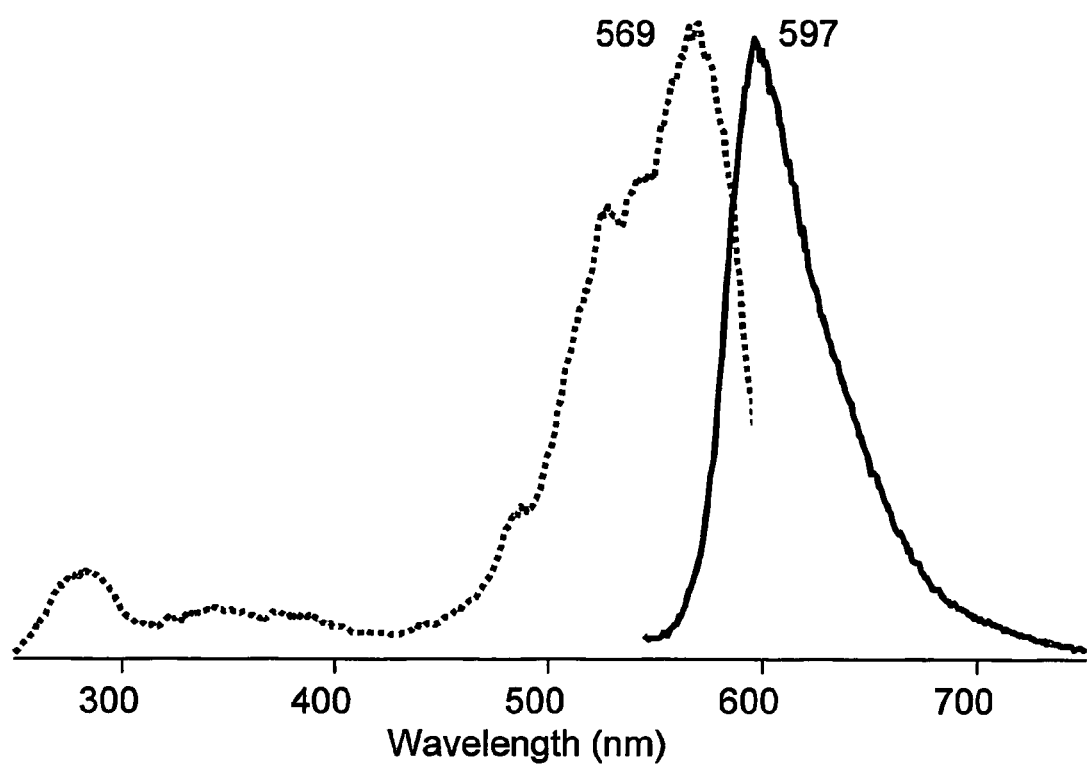
FIG. 7 illustrates the excitation-emission spectra for wild type hm2CP.

To facilitate protein purification, coding region of hm2CP was cloned into pQE30 expressing vector (Qiagen), so that recombinant protein contained six-histidine tag at its N-terminus. After expression in *E. coli* hm2CP was purified by metal-affinity resin TALON (Clontech). Absorption spectrum for purified hm2CP possessed single maximum at 568 nm (FIG. 6). Very weak red fluorescence (excitation maxima at 569 and 597 nm, respectively) of hm2CP can be detected (FIG. 7).

Example 5 hm2CP Mutagenesis

Figure 8:
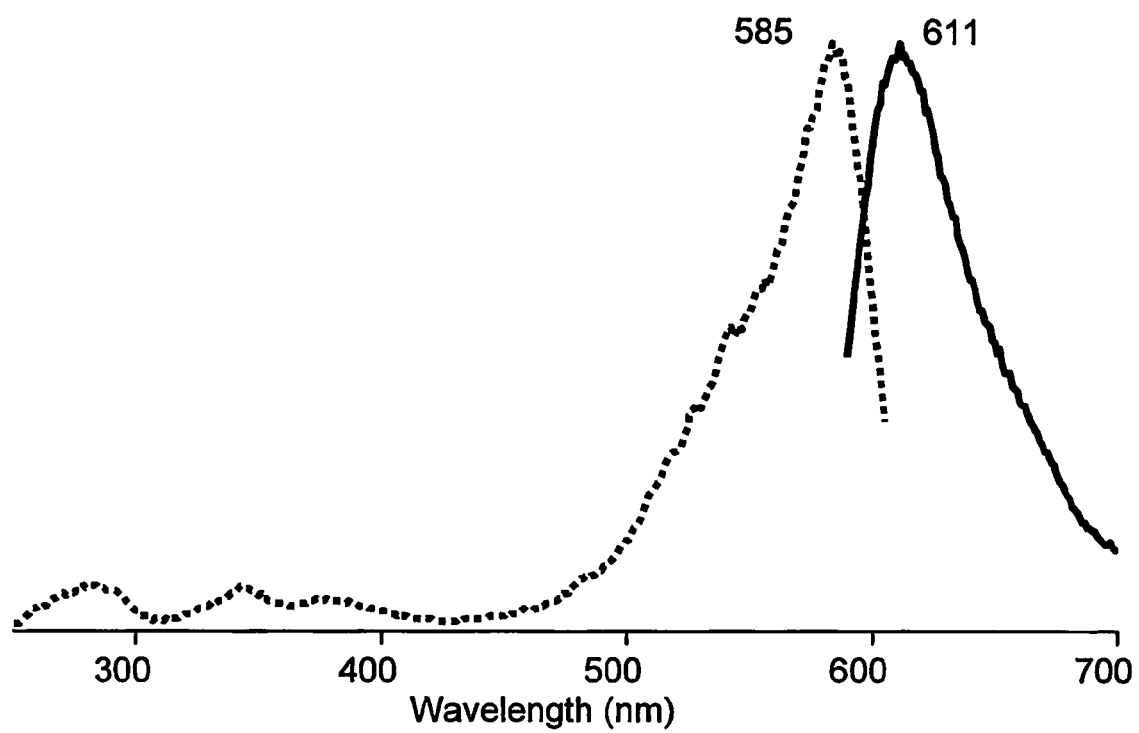
FIG. 8 illustrates the excitation-emission spectra for the red fluorescent mutant S3-2 of hm2CP.

The hm2CP nucleic acid coding sequence was prepared as described above in the Example 4. To generate fluorescent mutants of hm2CP we used random mutagenesis. The Diversity PCR Random Mutagenesis kit (Clontech) was used for random mutagenesis of hm2CP, under conditions optimal for 5-6 mutations per 1000 bp. E. coli colonies expressing mutant proteins were visually screened with a fluorescent stereomicroscope SZX-12 (Olympus). The brightest variants were selected and subjected to another round of random mutagenesis. Totally four rounds of the mutagenesis resulted in bright and fast maturing red fluorescent mutant designated as S3-2. Compared to the parental chromoprotein, S3-2 carried 13 amino acid substitutions, specifically D24G, B30V, K73R, T91S, I118V, K136R, T145N, S154P, C161A, Y162F, L181M, V199T, I201T (SEQ ID NOs: 15, 16, and 30). Excitation and emission spectra for this mutant possessed maxima at 585 and 611 nm, respectively (FIG. 8). S3-2 red fluorescent protein has a monomeric nature as revealed by gel-filtration data. To enhance expression in mammalian cells we synthesized "humanized" version of the S3-2 using mammalian-optimised codons (SEQ ID NOs: 21, 22, and 33).

Example 6

Polyclonal Antibody Preparation

Coding regions of nucleic acids of S3-2 red fluorescent protein and Phi-YFP-M1 yellow fluorescent protein prepared as described above in the Examples 2 and 5, respectively, were cloned into pQE30 expressing vector (Qiagen), so that recombinant proteins contained six-histidine tag at its N-terminus. After expression in E. coli hm2CP was purified by metal-affinity resin TALON (Clontech) under denaturing conditions. Rabbits were immunized and boosted four times at monthly intervals with recombinant DSN polypeptide emulsified in complete Freund's adjuvant Ten or 11 days after each boost the animals were bled. Polyclonal antiserum was tested on recombinant protein by ELISA and by Western immunobloting.

Example 7

Mammalian Cell Labeling Using PhiYFP and S3-2 Protein.

For fluorescent labelling of eukaryotic cells, the humanised versions of phiYFP-M1 and S3-2 protein prepared as described above in the Examples 2 and 5, respectively, were cloned into pEGFP-C1 vector (CLONTECH) between AgeI and BglII restriction sites (in lieu of the EGFP-coding region). The following cell lines were used: 293T human kidney epithelial cells, 3T3 mouse embryo fibroblasts, L929 murine subcutaneous fibroblasts, Vero African green monkey kidney epithelial cells and COS1 African green monkey kidney fibroblasts. Cells were transfected using LipofectAMINE reagent (Invitrogen) and were tested 20 h after transfection. An Olympus CK40 fluorescence microscope equipped with a CCD camera (DP-50, Olympus) was used for cell imaging. Expression of phiYFP-M1 or S3-2 in different cell lines resulted in bright yellow or red signals without aggregation. Fluorescence was clearly detectable 24 hours after tnansfection. No cell toxicity was observed.

Example 8

Protein Labeling and Protein Localization Analysis Using PhiYFP and S3-2 Protein.

The humanised versions of phiYFP-M1 and S3-2 protein prepared as described above in the Examples 2 and 5, respectively, were fused to human cytoplasmic beta-actin. Transfection of 293T human kidney epithelial cells with plasmids expressing phiYFP-M1 or S3-2 -tagged fused constructs resulted in bright fluorescence that revealed pattern closely agreed to that observed for fusions with EGFP.

The humanised version of phiYFP-M1 was further fused to human alpha tubulin and nucleolar protein, fibrillarin. 293T human kidney epithelial cells transfected by plasmids expressing phiYFP-M1-tagged fused constructs resulted in bright fluorescence with pattern characteristic for the correspondent fusion partners.

Example 9

Mitochondrion Labeling Using PhiYFP

Coding sequence of the humanised phiYFP-M1 version prepared as described above in the Example 2 was fused with mitochondrial targeting sequence (MTS) from subunit VIII of human cytochrome c oxidase. Transfection of 293T human kidney epithelial cells with plasmids expressing phiYFP-M1-MTS fused construct resulted in effective translocation of the protein to the mitochondria of host cells. Fluorescence was clearly detectable 24 hours after transfection.

Example 10

Golgi Apparatus Labeling Using PhiYFP

Coding sequence of the humanised phiYFP-M1 version prepared as described above in the Example 2 was fused with a sequence encoding the N-terminal 81 amino acids of human beta 1,4-galactosyltransferase (GT; Watzele & Berger (1990) Nucleic Acids. Res. 18:7174). This region of human beta 1, 4-GT contains the membrane-anchoring signal peptide that targets the fusion protein to the trans-medial region of the Golgi apparatus (Llopis et al. Proc. Natl. Acad. Sci. USA (1998) 95: 6803-6808; Yamaguchi & Fukuda J. Biol. Chem. (1995)270: 12170-12176; Gleeson et al. Glycoconjugate J. (1994) 11: 381-394). Transfection of 293T human kidney epithelial cells with plasmids expressing phiYFP-M1-tagged fused construct resulted in fluorescent labeling of the trans-medial region of the Golgi apparatus in the cells.

Example 11

Peroxisome Labeling Using PhiYFP

Coding sequence of the humanised phiYFP-M1 version prepared as described above in the Example 2 was fused with a peroximal targeting signal 1 (PTS1). The PTS1 sequence encodes the tripeptide SKL, which targets the fusion protein to the matrix of peroxisomes (Gould et al. J. Biol. Chem. (1989) 108: 1657-1664; Gould et al. EMBO J. (1990) 9: 85-90; Monosov et al. J. Histo. Cytochem. (1996) 44: 581-589). Transfection of 293T human kidney epithelial cells with plasmids expressing phiYFP-M1 -tagged fused construct resulted in fluorescent labeling of the peroxisomes.

Example 12

Nucleus Labeling Using PhiYFP

Coding sequence of the humanised phiYFP-M1 version prepared as described above in the Example 2 was fused with three copies of the nuclear localization signal (NLS) of the simian virus 40 large T-antigen fused at its C-terminus (Kalderon et al. Cell (1984) 39: 499-509; Lanford et al. Cell (1986) 46: 575-582). Transfection of 293T human kidney epithelial cells with plasmids expressing phiYFP-M1 -tagged fused construct resulted in fluorescent labeling of the nucleuses.

All publications and patent applications cited in this specification are incorporated by reference herein as if each individual publication or patent application were specifically and individually indicated to be incorporated by reference. The citation of any publication is to provide context and understanding of the present invention and should not be construed as an admission that any such publication is prior art.

What is claimed is:

1. An isolated nucleic acid molecule encoding a fluorescent protein, wherein said protein has at least 90% identity with full length SEQ ID NO: 10.

2. A vector comprising the nucleic acid molecule according to claim 1.

3. An expression cassette comprising
   (a) a transcriptional initiation region that is functional in an expression host;
   (b) the nucleic acid molecule according to claim 1; and
   (c) a transcriptional termination region functional in said expression host.

4. An isolated host cell or progeny thereof, comprising the expression cassette according to claim 3 as part of an extrachromosomal element or integrated into the genome of a host cell as a result of introduction of said expression cassette into said host cell.

5. An isolated transgenic cell, or progeny thereof, comprising the nucleic acid molecule according to claim 1.

6. The nucleic acid molecule according to claim 1, wherein said nucleic acid comprises a sequence that is identical to a nucleotide sequence of at least 300 contiguous nucleotides in length of SEQ ID NO:9.

7. A kit comprising at least one nucleic acid molecule according to claim 1.

8. The nucleic acid molecule according to the claim 1 which encodes full length SEQ ID NO: 10.

9. The nucleic acid molecule according to claim 1, wherein said nucleic acid molecule has a nucleotide sequence consisting of full length SEQ ID NO: 9.

10. The nucleic acid molecule according to claim 1, wherein said nucleic acid molecule has a nucleotide sequence having at least 95% identity with full length SEQ ID NO:9.

11. A method for producing a fluorescent protein, said method comprising
   (a) introducing the expression cassette according to claim 3 to an isolated host cell,
   (b) expressing the fluorescent protein from the nucleic acid molecule, and
   (c) isolating the protein substantially free of other proteins.

* * * * *

SEQUENCE LISTING

<160> NUMBER OF SEQ ID NOS: 23

<210> SEQ ID NO 1
<211> LENGTH: 784
<212> TYPE: DNA
<213> ORGANISM: Phialidium sp.

<400> SEQUENCE: 1

```
gaactgataa aagaaatcat catcatgtct agtggagcac tgttgttcca cggaaagatc    60
ccatatgttg ttgagatgga gggaaatgtt gatggacaca cattctccat tagaggtaaa   120
ggttatggag atgcaagtgt tggtaaagtt gatgcccaat tcatctgcac aactggagat   180
gtaccagttc catggtcaac tttagtaaca acacttactt atggtgcaca atgcttcgcc   240
aaatatggtc cagaattaaa ggatttctac aagagttgca tgcctgaagg ctatgtgcag   300
gagcgtacaa tcacatttga aggggacgga gtatttaaaa ctcgcgctga agttacattt   360
gaaaacggat ctgtttataa ccgagtcaaa cttaatggac aaggatttaa gaaagacgga   420
catgtgcttg gaaagaatct tgaattcaat ttcacacctc attgtcttta catttgggga   480
gatcaggcta atcatggttt gaagtctgct ttcaaaatta tgcatgagat tactggatca   540
aaagaagact tcattgttgc agaccacacc caaatgaaca cacccattgg tggtggacca   600
gtccatgtcc ctgaatacca tcatataaca taccatgtca ctctcagcaa agatgttact   660
gatcacaggg ataacatgag cttggttgaa accgtacggg ctgtggattg cagaaaaaca   720
tatctttaaa ttgtaaattt atttgtagtt gaaaaccttt tgtcacgata tacccttta   780
ttat                                                               784
```

<210> SEQ ID NO 2
<211> LENGTH: 234
<212> TYPE: PRT
<213> ORGANISM: Phialidium sp.

<400> SEQUENCE: 2

```
Met Ser Ser Gly Ala Leu Leu Phe His Gly Lys Ile Pro Tyr Val Val
1               5                   10                  15
Glu Met Glu Gly Asn Val Asp Gly His Thr Phe Ser Ile Arg Gly Lys
            20                  25                  30
Gly Tyr Gly Asp Ala Ser Val Gly Lys Val Asp Ala Gln Phe Ile Cys
        35                  40                  45
Thr Thr Gly Asp Val Pro Val Pro Trp Ser Thr Leu Val Thr Thr Leu
    50                  55                  60
Thr Tyr Gly Ala Gln Cys Phe Ala Lys Tyr Gly Pro Glu Leu Lys Asp
65                  70                  75                  80
Phe Tyr Lys Ser Cys Met Pro Glu Gly Tyr Val Gln Glu Arg Thr Ile
                85                  90                  95
Thr Phe Glu Gly Asp Gly Val Phe Lys Thr Arg Ala Glu Val Thr Phe
            100                 105                 110
Glu Asn Gly Ser Val Tyr Asn Arg Val Lys Leu Asn Gly Gln Gly Phe
        115                 120                 125
Lys Lys Asp Gly His Val Leu Gly Lys Asn Leu Glu Phe Asn Phe Thr
    130                 135                 140
Pro His Cys Leu Tyr Ile Trp Gly Asp Gln Ala Asn His Gly Leu Lys
145                 150                 155                 160
Ser Ala Phe Lys Ile Met His Glu Ile Thr Gly Ser Lys Glu Asp Phe
                165                 170                 175
```

Ile Val Ala Asp His Thr Gln Met Asn Thr Pro Ile Gly Gly Pro
            180                 185                 190

Val His Val Pro Glu Tyr His His Ile Thr Tyr His Val Thr Leu Ser
            195                 200                 205

Lys Asp Val Thr Asp His Arg Asp Asn Met Ser Leu Val Glu Thr Val
        210                 215                 220

Arg Ala Val Asp Cys Arg Lys Thr Tyr Leu
225                 230

<210> SEQ ID NO 3
<211> LENGTH: 705
<212> TYPE: DNA
<213> ORGANISM: Artificial sequence
<220> FEATURE:
<223> OTHER INFORMATION: phiYFP-Y1 mutant of the phiYFP

<400> SEQUENCE: 3
atgcctagtg gagcactgtt gttccacgga aagatcccat atgttgttga gatggaggga      60
aatgttgatg gacacacatt ctccattaga ggtaaaggtt atggagatgc aagtgttggt     120
aaagttgatg cccaattcat ctgcacaact ggagatgtac cagttccatg gtcaacttta     180
gtaacaacac ttacttatgg tgcacaatgc ttcgccaaat atggtccaga attaaaggat     240
ttctacaaga gttgcatgcc tgaaggctat gtgcaggagc gtacaatcac atttgaaggg     300
gacggagtat ttaaaactcg cgctgaagtt acatttgaaa acggatctgt ttataaccga     360
gtcaaactta tggacaagg atttaagaaa gacggacatg tgcttggaaa gaatcttgaa      420
ttcaatttca cacctcattg tctttacatt tggggagatc aggctaatca tggtttgaag     480
tctgctttca aaattatgca tgagattact ggatcaaaag gagacttcat tgttgcagac     540
cacacccaaa tgaacacacc cattggtggt ggaccagtcc atgtccctga ataccatcat     600
atgacatacc atgtcactct cagcaaagat gttactgatc acagggataa catgagcttg     660
gttgaaaccg tacgggctgt ggattgcaga aaaacatatc tttaa                     705

<210> SEQ ID NO 4
<211> LENGTH: 234
<212> TYPE: PRT
<213> ORGANISM: Artificial sequence
<220> FEATURE:
<223> OTHER INFORMATION: phiYFP-Y1 mutant of the phiYFP

<400> SEQUENCE: 4

Met Pro Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
        35                  40                  45

Thr Thr Gly Asp Val Pro Val Pro Trp Ser Thr Leu Val Thr Thr Leu
    50                  55                  60

Thr Tyr Gly Ala Gln Cys Phe Ala Lys Tyr Gly Pro Glu Leu Lys Asp
65                  70                  75                  80

Phe Tyr Lys Ser Cys Met Pro Glu Gly Tyr Val Gln Glu Arg Thr Ile
                85                  90                  95

Thr Phe Glu Gly Asp Gly Val Phe Lys Thr Arg Ala Glu Val Thr Phe
            100                 105                 110

Glu Asn Gly Ser Val Tyr Asn Arg Val Lys Leu Asn Gly Gln Gly Phe
        115                 120                 125

Lys Lys Asp Gly His Val Leu Gly Lys Asn Leu Glu Phe Asn Phe Thr
            130                 135                 140

Pro His Cys Leu Tyr Ile Trp Gly Asp Gln Ala Asn His Gly Leu Lys
145                 150                 155                 160

Ser Ala Phe Lys Ile Met His Glu Ile Thr Gly Ser Lys Gly Asp Phe
                165                 170                 175

Ile Val Ala Asp His Thr Gln Met Asn Thr Pro Ile Gly Gly Gly Pro
            180                 185                 190

Val His Val Pro Glu Tyr His Met Thr Tyr His Val Thr Leu Ser
        195                 200                 205

Lys Asp Val Thr Asp His Arg Asp Asn Met Ser Leu Val Glu Thr Val
    210                 215                 220

Arg Ala Val Asp Cys Arg Lys Thr Tyr Leu
225                 230

<210> SEQ ID NO 5
<211> LENGTH: 705
<212> TYPE: DNA
<213> ORGANISM: Artificial sequence
<220> FEATURE:
<223> OTHER INFORMATION: phiYFP-M0 mutant of the phiYFP

<400> SEQUENCE: 5
atgcctagtg gagcactgtt gttccacgga aagatcccat atgttgttga gatggaggga      60
aatgttgatg gacacacatt ctccattaga ggtaaaggtt atggagatgc aagtgttggt     120
aaagttgatg cccaattcat ctgcacaact ggagatgtac cagttccatg gtcaacttta     180
gtaacaacac ttacttatgg tgcacaatgc ttcgccaaat atggtccaga attaaaggat     240
ttctacaaga gttgcatgcc tgaaggctat gtgcaggagc gtacaatcac atttgaaggg     300
gacggaaact ttaaaactcg cgctgaagtt acatttgaaa acggatctgt ttataaccga     360
gtcaaactta atggacaagg atttaagaaa acggacatg tgcttggaaa gaatcttgaa      420
ttcaatttca cacctcattg tctttacatt tggggagatc aggctaatca tggtttgaag     480
tctgctttca aaattcgcca tgagattact ggatcaaaag gagacttcat tgttgcagac     540
cacacccaaa tgaacacacc cattggtggt ggaccagtcc atgtccctga aaaccatcat    600
atgagctacc atgtcaagct cagcaaagat gttactgatc acagggataa catgagcttg     660
aaggaaaccg tacgggctgt ggattgcaga aaaacatatc tttaa                    705

<210> SEQ ID NO 6
<211> LENGTH: 234
<212> TYPE: PRT
<213> ORGANISM: Artificial sequence
<220> FEATURE:
<223> OTHER INFORMATION: phiYFP-M0  mutant of the phiYFP

<400> SEQUENCE: 6

Met Pro Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
        35                  40                  45

Thr Thr Gly Asp Val Pro Val Pro Trp Ser Thr Leu Val Thr Thr Leu
    50                  55                  60

Thr Tyr Gly Ala Gln Cys Phe Ala Lys Tyr Gly Pro Glu Leu Lys Asp
65                  70                  75                  80

```
Phe Tyr Lys Ser Cys Met Pro Glu Gly Tyr Val Gln Glu Arg Thr Ile
                85                  90                  95

Thr Phe Glu Gly Asp Gly Asn Phe Lys Thr Arg Ala Glu Val Thr Phe
            100                 105                 110

Glu Asn Gly Ser Val Tyr Asn Arg Val Lys Leu Asn Gly Gln Gly Phe
        115                 120                 125

Lys Lys Asp Gly His Val Leu Gly Lys Asn Leu Glu Phe Asn Phe Thr
130                 135                 140

Pro His Cys Leu Tyr Ile Trp Gly Asp Gln Ala Asn His Gly Leu Lys
145                 150                 155                 160

Ser Ala Phe Lys Ile Arg His Glu Ile Thr Gly Ser Lys Gly Asp Phe
                165                 170                 175

Ile Val Ala Asp His Thr Gln Met Asn Thr Pro Ile Gly Gly Gly Pro
            180                 185                 190

Val His Val Pro Glu Asn His His Met Ser Tyr His Val Lys Leu Ser
        195                 200                 205

Lys Asp Val Thr Asp His Arg Asp Asn Met Ser Leu Lys Glu Thr Val
210                 215                 220

Arg Ala Val Asp Cys Arg Lys Thr Tyr Leu
225                 230
```

<210> SEQ ID NO 7
<211> LENGTH: 705
<212> TYPE: DNA
<213> ORGANISM: Artificial sequence
<220> FEATURE:
<223> OTHER INFORMATION: phiYFP-M1 mutant of the phiYFP

<400> SEQUENCE: 7

```
atgtctagtg gagcactgtt gttccacgga aagatcccat atgttgttga gatggaggga      60
aatgttgatg gacacacatt ctccattaga ggtaaaggtt atggagatgc aagtgttggt     120
aaagttgatg cccaattcat ctgcacaact ggagatgtac cagttccatg gtcaacttta     180
gtaacaacac ttacttatgg tgcacaatgc ttcgccaaat atggtccaga attaaaggat     240
ttctacaaga gttgcatgcc tgatggctat gtgcaggagc gtacaatcac atttgaaggg     300
gacggaaact ttaaaactcg cgctgaagtt acatttgaaa acggatctgt ttataaccga     360
gtcaaactta atggacaagg atttaagaaa gacggacatg tgcttggaaa gaatcttgaa     420
ttcaatttca cacctcattg tctttacatt tggggagatc aggctaatca tggtttgaag     480
tctgctttca aaatttgcca tgagattact ggatcaaaag gagacttcat tgttgcagac     540
cacacccaaa tgaacacacc cattggtggt ggaccagtcc atgtccctga ataccatcat     600
atgagctacc atgtcaagct cagcaaagat gttactgatc acagggataa catgagcttg     660
aaggaaaccg tacgggctgt ggattgcaga aaaacatatc tttaa                     705
```

<210> SEQ ID NO 8
<211> LENGTH: 234
<212> TYPE: PRT
<213> ORGANISM: Artificial sequence
<220> FEATURE:
<223> OTHER INFORMATION: phiYFP-M1 mutant of the phiYFP

<400> SEQUENCE: 8

```
Met Ser Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30
```

Gly Tyr Gly Asp Ala Ser Val Gly Lys Val Asp Ala Gln Phe Ile Cys
            35                  40                  45

Thr Thr Gly Asp Val Pro Val Pro Trp Ser Thr Leu Val Thr Thr Leu
 50                  55                  60

Thr Tyr Gly Ala Gln Cys Phe Ala Lys Tyr Gly Pro Glu Leu Lys Asp
 65                  70                  75                  80

Phe Tyr Lys Ser Cys Met Pro Asp Gly Tyr Val Gln Glu Arg Thr Ile
                 85                  90                  95

Thr Phe Glu Gly Asp Gly Asn Phe Lys Thr Arg Ala Glu Val Thr Phe
                100                 105                 110

Glu Asn Gly Ser Val Tyr Asn Arg Val Lys Leu Asn Gly Gln Gly Phe
            115                 120                 125

Lys Lys Asp Gly His Val Leu Gly Lys Asn Leu Glu Phe Asn Phe Thr
130                 135                 140

Pro His Cys Leu Tyr Ile Trp Gly Asp Gln Ala Asn His Gly Leu Lys
145                 150                 155                 160

Ser Ala Phe Lys Ile Cys His Glu Ile Thr Gly Ser Lys Gly Asp Phe
                165                 170                 175

Ile Val Ala Asp His Thr Gln Met Asn Thr Pro Ile Gly Gly Gly Pro
                180                 185                 190

Val His Val Pro Glu Tyr His Met Ser Tyr His Val Lys Leu Ser
            195                 200                 205

Lys Asp Val Thr Asp His Arg Asp Asn Met Ser Leu Lys Glu Thr Val
210                 215                 220

Arg Ala Val Asp Cys Arg Lys Thr Tyr Leu
225                 230

<210> SEQ ID NO 9
<211> LENGTH: 705
<212> TYPE: DNA
<213> ORGANISM: Artificial sequence
<220> FEATURE:
<223> OTHER INFORMATION: humanized version of the phiYFP-M1

<400> SEQUENCE: 9
atgagcagcg gcgccctgct gttccacggc aagatcccct acgtggtgga gatggagggc      60
aatgtggatg ccacaccttc agcatccgc ggcaagggct acggcgatgc cagcgtgggc      120
aaggtggatg cccagttcat ctgcaccacc ggcgatgtgc ccgtgccctg gagcaccctg      180
gtgaccaccc tgacctacgg cgcccagtgc ttcgccaagt acggccccga gctgaaggat      240
ttctacaaga gctgcatgcc cgatggctac gtgcaggagc gcaccatcac cttcgagggc      300
gatggcaatt tcaagacccg cgccgaggtg accttcgaga atggcagcgt gtacaatcgc      360
gtgaagctga atggccaggg cttcaagaag gatggccacg tgctgggcaa gaatctggag      420
ttcaatttca ccccccactg cctgtacatc tggggcgatc aggccaatca cggcctgaag      480
agcgccttca gatctgcca cgagatcacc ggcagcaagg gcgatttcat cgtggccgat      540
cacacccaga tgaatacccc catcggcggc ggccccgtgc acgtgcccga gtaccaccac      600
atgagctacc acgtgaagct gagcaaggat gtgaccgatc accgcgataa tatgagcctg      660
aaggagaccg tgcgcgccgt ggattgccgc aagacctacc tgtga                    705

<210> SEQ ID NO 10
<211> LENGTH: 234
<212> TYPE: PRT
<213> ORGANISM: Artificial sequence
<220> FEATURE:

<223> OTHER INFORMATION: humanized version of the phiYFP-M1

<400> SEQUENCE: 10

```
Met Ser Ser Gly Ala Leu Leu Phe His Gly Lys Ile Pro Tyr Val Val
1               5                   10                  15
Glu Met Glu Gly Asn Val Asp Gly His Thr Phe Ser Ile Arg Gly Lys
            20                  25                  30
Gly Tyr Gly Asp Ala Ser Val Gly Lys Val Asp Ala Gln Phe Ile Cys
        35                  40                  45
Thr Thr Gly Asp Val Pro Val Pro Trp Ser Thr Leu Val Thr Thr Leu
    50                  55                  60
Thr Tyr Gly Ala Gln Cys Phe Ala Lys Tyr Gly Pro Glu Leu Lys Asp
65                  70                  75                  80
Phe Tyr Lys Ser Cys Met Pro Asp Gly Tyr Val Gln Glu Arg Thr Ile
                85                  90                  95
Thr Phe Glu Gly Asp Gly Asn Phe Lys Thr Arg Ala Glu Val Thr Phe
            100                 105                 110
Glu Asn Gly Ser Val Tyr Asn Arg Val Lys Leu Asn Gly Gln Gly Phe
        115                 120                 125
Lys Lys Asp Gly His Val Leu Gly Lys Asn Leu Glu Phe Asn Phe Thr
    130                 135                 140
Pro His Cys Leu Tyr Ile Trp Gly Asp Gln Ala Asn His Gly Leu Lys
145                 150                 155                 160
Ser Ala Phe Lys Ile Cys His Glu Ile Thr Gly Ser Lys Gly Asp Phe
                165                 170                 175
Ile Val Ala Asp His Thr Gln Met Asn Thr Pro Ile Gly Gly Gly Pro
            180                 185                 190
Val His Val Pro Glu Tyr His His Met Ser Tyr His Val Lys Leu Ser
        195                 200                 205
Lys Asp Val Thr Asp His Arg Asp Asn Met Ser Leu Lys Glu Thr Val
    210                 215                 220
Arg Ala Val Asp Cys Arg Lys Thr Tyr Leu
225                 230
```

<210> SEQ ID NO 11
<211> LENGTH: 1047
<212> TYPE: DNA
<213> ORGANISM: Anthomedusae species
<220> FEATURE:
<221> NAME/KEY: misc_feature
<223> OTHER INFORMATION: hydromedusa 1 from sub-order Anthomedusae

<400> SEQUENCE: 11

```
cttttcttaa aaagaattca aaaggacgg tttactagac atacttatac agctttactt      60
ataaggaag aaatgaatgt gatgcgttac aacagaggat tctgcagagt tttgcaaaat    120
ggtgtcaaaa atttacgttc tagaaattgc agtacggaag aaaaacccgt catacttggt    180
gcaatgacag aaacatttca gaaaaaattg ccatataagt tagaattgga tggagatgtt    240
gatgggcaaa catttaaggt tattggtgag ggcgttgggg atgcaaccac tggtgtaatt    300
gaaggaaaat atgtttgtac agaaggagaa gttcctattt catgggtttc gctcatcacc    360
tcattaagtt atggtgcgaa atgttttgtt cgatatccaa atgaaataaa tgatttttc    420
aaaagtactt ttccttctgg atatcatcaa gaaagaaaaa ttacatatga gaatgatggt    480
gttttagaaa cagcagctaa aattactatg gaagtggtg caatagtgaa tagaataaat    540
gtgaaaggca caggcttcga taagatggt catgtatgcc aaaaaaatct tgaatcctcc    600
```

```
cctccttcga caacatatgt tgttcccgag ggagaaggta ttcgaatcat ctatagaaac    660
atctatccaa caaagatgg tcactatgtt gttgccgaca cacagcaagt aaatcgacca    720
attagagcac aaggaacatc agctatccca acatatcatc acattaaatc gaaagttgat    780
ctttcaacag atccgaaga aaataaagat catattatca tcaaagaaac caactgcgca    840
tttgacgctg attttcttta agatttccga tttgcatcaa gattgaaaaa ctaaataaag    900
ataggtaaaa aaaatatgtc tttgatgtta catacagtat tgatataagc ttcaaagaaa    960
tatattttca aataaacttt ataaaattag gaatctttga atatataaac taaacctttt   1020
atttgtagaa taaaaataat taaagac                                       1047
```

<210> SEQ ID NO 12
<211> LENGTH: 262
<212> TYPE: PRT
<213> ORGANISM: Anthomedusae species
<220> FEATURE:
<221> NAME/KEY: misc_feature
<223> OTHER INFORMATION: hydromedusa 1 from sub-order Anthomedusae

<400> SEQUENCE: 12

```
Met Asn Val Met Arg Tyr Asn Arg Gly Phe Cys Arg Val Leu Gln Asn
1               5                   10                  15

Gly Val Lys Asn Leu Arg Ser Arg Asn Cys Ser Thr Glu Glu Lys Pro
            20                  25                  30

Val Ile Leu Gly Ala Met Thr Glu Thr Phe Gln Lys Lys Leu Pro Tyr
        35                  40                  45

Lys Leu Glu Leu Asp Gly Asp Val Asp Gly Gln Thr Phe Lys Val Ile
    50                  55                  60

Gly Glu Gly Val Gly Asp Ala Thr Thr Gly Val Ile Glu Gly Lys Tyr
65                  70                  75                  80

Val Cys Thr Glu Gly Glu Val Pro Ile Ser Trp Val Ser Leu Ile Thr
                85                  90                  95

Ser Leu Ser Tyr Gly Ala Lys Cys Phe Val Arg Tyr Pro Asn Glu Ile
            100                 105                 110

Asn Asp Phe Phe Lys Ser Thr Phe Pro Ser Gly Tyr His Gln Glu Arg
        115                 120                 125

Lys Ile Thr Tyr Glu Asn Asp Gly Val Leu Glu Thr Ala Ala Lys Ile
    130                 135                 140

Thr Met Glu Ser Gly Ala Ile Val Asn Arg Ile Asn Val Lys Gly Thr
145                 150                 155                 160

Gly Phe Asp Lys Asp Gly His Val Cys Gln Lys Asn Leu Glu Ser Ser
                165                 170                 175

Pro Pro Ser Thr Thr Tyr Val Val Pro Glu Gly Glu Gly Ile Arg Ile
            180                 185                 190

Ile Tyr Arg Asn Ile Tyr Pro Thr Lys Asp Gly His Tyr Val Val Ala
        195                 200                 205

Asp Thr Gln Gln Val Asn Arg Pro Ile Arg Ala Gln Gly Thr Ser Ala
    210                 215                 220

Ile Pro Thr Tyr His His Ile Lys Ser Lys Val Asp Leu Ser Thr Asp
225                 230                 235                 240

Pro Glu Glu Asn Lys Asp His Ile Ile Ile Lys Glu Thr Asn Cys Ala
                245                 250                 255

Phe Asp Ala Asp Phe Ser
            260
```

<210> SEQ ID NO 13

```
<211> LENGTH: 1089
<212> TYPE: DNA
<213> ORGANISM: Anthomedusae species
<220> FEATURE:
<221> NAME/KEY: misc_feature
<223> OTHER INFORMATION: hydromedusa 2 from sub-order Anthomedusae

<400> SEQUENCE: 13
atcattcgct gatacgaagt gaaagtagcg tttgctgaaa gcttcctgga attgctccta       60
cgtatcttga aagttgctcc tacgctccaa cttgtttgtt caaaatggaa ggtggtccag      120
cattatttca atccgatatg acattcaaga tcttcatcga tggagtggtg aatgatcaga      180
aattcacgat aatcgcagat ggatcgtcca aattcccca tggtgacttc aacgtgcatg      240
ctgtgtgcga aaccgggaaa ctcccaatgt catggaaacc tatttgtcac cttatccaat      300
acggggagcc attctttgca aaatatccca atggcatcag ccattttgca caggagtgct      360
ttccagaagg attaacaatt gatcgaacag tcagattcga aaatgacggc actatgacgt      420
ctcaccacac ctatgagttg gacggcacct gtgtcatttc caggataacc gttaattgtg      480
acggatttca acctgatgga ccaatcatga agaccagct tgttgatatc ctgccaactg       540
agacacatat gttccctcat gggtccaatg ctgtcagaca attgtgctac attggcttca      600
cgacagctga tggtggtctc atgatgtcac attttgattc gaaattgaca ttcaatggtt      660
cgagagcaat caagattcct ggacctcatt tcgttactgt gataatcaaa cagatgaaag      720
atacaagcga caagcgtgat catgtgtgtc aacgtgaagt cacctacgct cactcagttc      780
cacgcatcac ttctgctatc taaacatcat tcttaaaagg ggaacatgca catcatactt      840
cagtgtgagg gtcagtgtga gggtctttag atgtcaattt gtcgcaggtg tcacacggcg      900
tcgtttagat gttgaaggac gaaatgcgac aaagagatta atagagactc atatttttat      960
gtagaatcga ttcattcagc ccattggtaa cctttttggt attttatcat cttattattg     1020
tattggcact tgtttatat tttgtatgta atgtgtaaac aattgttgaa atacatgtc      1080 aagaacttg                                                            1089

<210> SEQ ID NO 14
<211> LENGTH: 232
<212> TYPE: PRT
<213> ORGANISM: Anthomedusae species
<220> FEATURE:
<221> NAME/KEY: misc_feature
<223> OTHER INFORMATION: hydromedusa 2 from sub-order Anthomedusae

<400> SEQUENCE: 14

Met Glu Gly Gly Pro Ala Leu Phe Gln Ser Asp Met Thr Phe Lys Ile
1               5                   10                  15

Phe Ile Asp Gly Val Val Asn Asp Gln Lys Phe Thr Ile Ile Ala Asp
            20                  25                  30

Gly Ser Ser Lys Phe Pro His Gly Asp Phe Asn Val His Ala Val Cys
        35                  40                  45

Glu Thr Gly Lys Leu Pro Met Ser Trp Lys Pro Ile Cys His Leu Ile
    50                  55                  60

Gln Tyr Gly Glu Pro Phe Phe Ala Lys Tyr Pro Asn Gly Ile Ser His
65                  70                  75                  80

Phe Ala Gln Glu Cys Phe Pro Glu Gly Leu Thr Ile Asp Arg Thr Val
                85                  90                  95

Arg Phe Glu Asn Asp Gly Thr Met Thr Ser His His Thr Tyr Glu Leu
            100                 105                 110

Asp Gly Thr Cys Val Ile Ser Arg Ile Thr Val Asn Cys Asp Gly Phe
```

```
                115                 120                 125
Gln Pro Asp Gly Pro Ile Met Lys Asp Gln Leu Val Asp Ile Leu Pro
            130                 135                 140

Thr Glu Thr His Met Phe Pro His Gly Ser Asn Ala Val Arg Gln Leu
145                 150                 155                 160

Cys Tyr Ile Gly Phe Thr Thr Ala Asp Gly Gly Leu Met Met Ser His
                165                 170                 175

Phe Asp Ser Lys Leu Thr Phe Asn Gly Ser Arg Ala Ile Lys Ile Pro
            180                 185                 190

Gly Pro His Phe Val Thr Val Ile Ile Lys Gln Met Lys Asp Thr Ser
                195                 200                 205

Asp Lys Arg Asp His Val Cys Gln Arg Glu Val Thr Tyr Ala His Ser
            210                 215                 220

Val Pro Arg Ile Thr Ser Ala Ile
225                 230

<210> SEQ ID NO 15
<211> LENGTH: 699
<212> TYPE: DNA
<213> ORGANISM: Artificial sequence
<220> FEATURE:
<223> OTHER INFORMATION: S3-2 mutant of the hm2CP from a hydromedusa 2
      from sub-order Anthomedusae

<400> SEQUENCE: 15
atggaaggtg gtccagcatt atttcaatcc gacatgacat tcaagatctt catcgatgga      60
gtggtgaatg gtcagaaatt cacgatagtc gcagatggat cgtccaaatt ccccccatggt    120 gacttcaacg tacatgctgt gtgcgaaacc gggaaactcc caatgtcatg gaaacccatt    180
tgtcacctta tccaatacgg ggagccattc tttgcaagat atcccaacgg catcagccat    240
tttgcacagg agtgctttcc agaaggatta tcaattgatc gaacagtcag attcgaaaat    300
gacggcacta tgacgtctca ccacacctat gagttggacg gcacctgtgt cgtttccagg    360
ataaccgtta attgtgacgg atttcaacct gatggaccaa tcatgagaga ccagcttgtt    420
gatatcctgc caaacgagac acatatgttc cctcatggac ccaatgctgt cagacaattg    480
gctttcatag gcttcacgac agctgatggt ggtctcatga tgtcacattt tgattcgaaa    540
atgacattca atggttcgag agcaatcaag attcctggac ctcatttcgt cactaccata    600
accaaacaga tgaaagatac aagcgacaag cgtgatcatg tgtgtcagcg ggaagtcacc    660
tacgctcact cagttccacg catcactttct gctatctaa                           699

<210> SEQ ID NO 16
<211> LENGTH: 232
<212> TYPE: PRT
<213> ORGANISM: Artificial sequence
<220> FEATURE:
<223> OTHER INFORMATION: S3-2 mutant of the hm2CP from a hydromedusa 2
      from sub-order Anthomedusae

<400> SEQUENCE: 16

Met Glu Gly Gly Pro Ala Leu Phe Gln Ser Asp Met Thr Phe Lys Ile
1               5                   10                  15

Phe Ile Asp Gly Val Val Asn Gly Gln Lys Phe Thr Ile Val Ala Asp
            20                  25                  30

Gly Ser Ser Lys Phe Pro His Gly Asp Phe Asn Val His Ala Val Cys
        35                  40                  45

Glu Thr Gly Lys Leu Pro Met Ser Trp Lys Pro Ile Cys His Leu Ile
    50                  55                  60
```

Gln Tyr Gly Glu Pro Phe Phe Ala Arg Tyr Pro Asn Gly Ile Ser His
65                  70                  75                  80

Phe Ala Gln Glu Cys Phe Pro Glu Gly Leu Ser Ile Asp Arg Thr Val
                85                  90                  95

Arg Phe Glu Asn Asp Gly Thr Met Thr Ser His His Thr Tyr Glu Leu
            100                 105                 110

Asp Gly Thr Cys Val Val Ser Arg Ile Thr Val Asn Cys Asp Gly Phe
        115                 120                 125

Gln Pro Asp Gly Pro Ile Met Arg Asp Gln Leu Val Asp Ile Leu Pro
    130                 135                 140

Asn Glu Thr His Met Phe Pro His Gly Pro Asn Ala Val Arg Gln Leu
145                 150                 155                 160

Ala Phe Ile Gly Phe Thr Thr Ala Asp Gly Gly Leu Met Met Ser His
                165                 170                 175

Phe Asp Ser Lys Met Thr Phe Asn Gly Ser Arg Ala Ile Lys Ile Pro
            180                 185                 190

Gly Pro His Phe Val Thr Thr Ile Thr Lys Gln Met Lys Asp Thr Ser
        195                 200                 205

Asp Lys Arg Asp His Val Cys Gln Arg Glu Val Thr Tyr Ala His Ser
    210                 215                 220

Val Pro Arg Ile Thr Ser Ala Ile
225                 230

<210> SEQ ID NO 17
<211> LENGTH: 705
<212> TYPE: DNA
<213> ORGANISM: Artificial sequence
<220> FEATURE:
<223> OTHER INFORMATION: phiYFP-M1G1 mutant, derived from humanized
      version of the phiYFP-M1

<400> SEQUENCE: 17
atgtccagcg gcgccctgct gttccacggc aagatcccct acgtggtgga gatggagggc    60
aatgtggatg ccacaccttt cagcatccgc ggcaagggct acggcgatgc cagcgtgggc   120
aaggtggatg cccagttcat ctgcaccacc ggcgatgtgc ccgtgccctg gagcaccctg   180
gtgaccaccc tgtcctacgg cgcccagtgc ttcgccaagt acggccccga gctgaaggat   240
ttctacaaga gctgcatgcc cgatggctac gtgcaggagc gcaccatcac cttcgagggc   300
gatggcaatt tcaagacccg cgccgaggtg accttcgaga atggcagcgt gtacaatcgc   360
gtgaagctga atggccaggg cttcaagaag gatggccacg tgctgggcaa gaatctggag   420
ttcaatttca ccccccactg ccagtacatc tggggcgatc aggccaatca cggcctgaag   480
agcgccttca agatctgcca cgagatcacc ggcagcaagg gcgatttcat cgtggccgat   540
cacacccaga tgaatacccc catcggcggc ggccccgtgc acgtgcccga gtaccaccac   600
atgagcaccc acgtgaagct gagcaaggat gtgaccgatc accgcgataa tatgagcctg   660
aaggagaccg tgcgcgccgt ggattgccga acagcctacc tgtga               705

<210> SEQ ID NO 18
<211> LENGTH: 234
<212> TYPE: PRT
<213> ORGANISM: Artificial sequence
<220> FEATURE:
<223> OTHER INFORMATION: phiYFP-M1G1 mutant, derived from humanized
      version of the phiYFP-M1

<400> SEQUENCE: 18

```
Met Ser Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
        35                  40                  45

Thr Thr Gly Asp Val Pro Val Pro Trp Ser Thr Leu Val Thr Thr Leu
    50                  55                  60

Ser Tyr Gly Ala Gln Cys Phe Ala Lys Tyr Gly Pro Glu Leu Lys Asp
65                  70                  75                  80

Phe Tyr Lys Ser Cys Met Pro Asp Gly Tyr Val Gln Glu Arg Thr Ile
                85                  90                  95

Thr Phe Glu Gly Asp Gly Asn Phe Lys Thr Arg Ala Glu Val Thr Phe
            100                 105                 110

Glu Asn Gly Ser Val Tyr Asn Arg Val Lys Leu Asn Gly Gln Gly Phe
        115                 120                 125

Lys Lys Asp Gly His Val Leu Gly Lys Asn Leu Glu Phe Asn Phe Thr
    130                 135                 140

Pro His Cys Gln Tyr Ile Trp Gly Asp Gln Ala Asn His Gly Leu Lys
145                 150                 155                 160

Ser Ala Phe Lys Ile Cys His Glu Ile Thr Gly Ser Lys Gly Asp Phe
                165                 170                 175

Ile Val Ala Asp His Thr Gln Met Asn Thr Pro Ile Gly Gly Gly Pro
            180                 185                 190

Val His Val Pro Glu Tyr His His Met Ser Thr His Val Lys Leu Ser
        195                 200                 205

Lys Asp Val Thr Asp His Arg Asp Asn Met Ser Leu Lys Glu Thr Val
    210                 215                 220

Arg Ala Val Asp Cys Arg Thr Ala Tyr Leu
225                 230

<210> SEQ ID NO 19
<211> LENGTH: 705
<212> TYPE: DNA
<213> ORGANISM: Artificial sequence
<220> FEATURE:
<223> OTHER INFORMATION: phiYFP-M1C1 mutant, derived from humanized
      version of the phiYFP-M1

<400> SEQUENCE: 19
atgtccagcg gcgcccagct gttccacggc aagatcccct acgtggtgga gatggagggc      60
aatgtggatg ccacaccttc cagcatccgc ggcaagggct acggcgatgc cagcgtgggc     120
aaggtggatg cccagttcat ctgcaccacc ggcgatgtgc ccgtgccctg gagcaccctg     180
gtgaccaccc tgtcctgggg cgcccagtgc ttcgccaagt acggccccga gctgaaggat     240
ttctacaaga gctgcatgcc cgatggctac gtgcaggagc gcaccatcac cttcgagggc     300
gatggcaatt tcaagacccg cgccgaggtg accttcgaga atggcagcgt gtacaatcgc     360
gtgaagctga aggccagggg cttcaagaag gatggccacg tgctgggcaa gaatctggag     420
ttcaatttca cccccccacta ccagtacatc tggggcgatc aggccaatca cggcctgaag     480
agcgccttca gatctgcca cgagatcacc ggcagtaagg gcgatttcat cgtggccgat     540
cacacccaga tgaataccccc catcggcggc ggccccgtgc acgtgcccga gtaccaccac     600
atgagcaccc acgtgaagct gagcaaggat gtgaccgatc accgcgataa tatgagcctg     660
aaggagacct gcgcgccgt ggattgccgc aagacctacc tgtga                      705
```

<210> SEQ ID NO 20
<211> LENGTH: 234
<212> TYPE: PRT
<213> ORGANISM: Artificial sequence
<220> FEATURE:
<223> OTHER INFORMATION: phiYFP-M1C1 mutant, derived from humanized version of the phiYFP-M1

<400> SEQUENCE: 20

```
Met Ser Ser Gly Ala Gln Leu Phe His Gly Lys Ile Pro Tyr Val Val
1               5                   10                  15
Glu Met Glu Gly Asn Val Asp Gly His Thr Phe Ser Ile Arg Gly Lys
            20                  25                  30
Gly Tyr Gly Asp Ala Ser Val Gly Lys Val Asp Ala Gln Phe Ile Cys
        35                  40                  45
Thr Thr Gly Asp Val Pro Val Pro Trp Ser Thr Leu Val Thr Thr Leu
    50                  55                  60
Ser Trp Gly Ala Gln Cys Phe Ala Lys Tyr Gly Pro Glu Leu Lys Asp
65                  70                  75                  80
Phe Tyr Lys Ser Cys Met Pro Asp Gly Tyr Val Gln Glu Arg Thr Ile
                85                  90                  95
Thr Phe Glu Gly Asp Gly Asn Phe Lys Thr Arg Ala Glu Val Thr Phe
            100                 105                 110
Glu Asn Gly Ser Val Tyr Asn Arg Val Lys Leu Lys Gly Gln Gly Phe
        115                 120                 125
Lys Lys Asp Gly His Val Leu Gly Lys Asn Leu Glu Phe Asn Phe Thr
    130                 135                 140
Pro His Tyr Gln Tyr Ile Trp Gly Asp Gln Ala Asn His Gly Leu Lys
145                 150                 155                 160
Ser Ala Phe Lys Ile Cys His Glu Ile Thr Gly Ser Lys Gly Asp Phe
                165                 170                 175
Ile Val Ala Asp His Thr Gln Met Asn Thr Pro Ile Gly Gly Gly Pro
            180                 185                 190
Val His Val Pro Glu Tyr His His Met Ser Thr His Val Lys Leu Ser
        195                 200                 205
Lys Asp Val Thr Asp His Arg Asp Asn Met Ser Leu Lys Glu Thr Leu
    210                 215                 220
Arg Ala Val Asp Cys Arg Lys Thr Tyr Leu
225                 230
```

<210> SEQ ID NO 21
<211> LENGTH: 699
<212> TYPE: DNA
<213> ORGANISM: Artificial sequence
<220> FEATURE:
<223> OTHER INFORMATION: humanized version of the S3-2 mutant of hm2CP from a hydromedusa 2 from sub-order Anthomedusae

<400> SEQUENCE: 21

```
atggagggcg cccccgccct gttccagagc gacatgacct caaaatctt  catcgacggc    60
gtggtgaacg ccagaagtt  caccatcgtg gccgacggca gcagcaagtt  cccccacggc   120
gacttcaacg tgcacgccgt gtgcgagacc ggcaagctgc ccatgagctg  gaagcccatc   180
tgccacctga tccagtacgg cgagcccttc ttcgcccgct accccaacgg  catcagccac   240
ttcgcccagg agtgcttccc cgagggcctg agcatcgacc gcaccgtgcg  cttcgagaac   300
gacggcacca tgaccagcca ccacacctac gagctggacg gcacctgcgt  ggtgagccgc   360
atcaccgtga actgcgacgg cttccagccc gacggcccca tcatgcgcga  ccagctggtg   420
```

```
gacatcctgc caacgagac ccacatgttc ccccacggcc ccaacgccgt gcgccagctg    480
gccttcatcg gcttcaccac cgccgacggc ggcctgatga tgagccactt cgacagcaag    540
atgaccttca acggcagccg cgccatcaag atccccggcc ccacttcgt gaccaccatc     600 accaagcaga tgaaggacac cagcgacaag cgcgaccacg tgtgccagcg cgaggtgacc    660
tacgcccaca gcgtgccccg catcaccagc gccatctga                           699
```

```
<210> SEQ ID NO 22
<211> LENGTH: 232
<212> TYPE: PRT
<213> ORGANISM: Artificial sequence
<220> FEATURE:
<223> OTHER INFORMATION: humanized S3-2 mutant of hm2CP from a
      hydromedusa 2 from sub-order Anthomedusae

<400> SEQUENCE: 22
```

Met Glu Gly Gly Pro Ala Leu Phe Gln Ser Asp Met Thr Phe Lys Ile
1               5                   10                  15

Phe Ile Asp Gly Val Val Asn Gly Gln Lys Phe Thr Ile Val Ala Asp
            20                  25                  30

Gly Ser Ser Lys Phe Pro His Gly Asp Phe Asn Val His Ala Val Cys
        35                  40                  45

Glu Thr Gly Lys Leu Pro Met Ser Trp Lys Pro Ile Cys His Leu Ile
    50                  55                  60

Gln Tyr Gly Glu Pro Phe Phe Ala Arg Tyr Pro Asn Gly Ile Ser His
65                  70                  75                  80

Phe Ala Gln Glu Cys Phe Pro Glu Gly Leu Ser Ile Asp Arg Thr Val
                85                  90                  95

Arg Phe Glu Asn Asp Gly Thr Met Thr Ser His His Thr Tyr Glu Leu
            100                 105                 110

Asp Gly Thr Cys Val Val Ser Arg Ile Thr Val Asn Cys Asp Gly Phe
        115                 120                 125

Gln Pro Asp Gly Pro Ile Met Arg Asp Gln Leu Val Asp Ile Leu Pro
    130                 135                 140

Asn Glu Thr His Met Phe Pro His Gly Pro Asn Ala Val Arg Gln Leu
145                 150                 155                 160

Ala Phe Ile Gly Phe Thr Thr Ala Asp Gly Gly Leu Met Met Ser His
                165                 170                 175

Phe Asp Ser Lys Met Thr Phe Asn Gly Ser Arg Ala Ile Lys Ile Pro
            180                 185                 190

Gly Pro His Phe Val Thr Thr Ile Thr Lys Gln Met Lys Asp Thr Ser
        195                 200                 205

Asp Lys Arg Asp His Val Cys Gln Arg Glu Val Thr Tyr Ala His Ser
    210                 215                 220

Val Pro Arg Ile Thr Ser Ala Ile
225                 230

```
<210> SEQ ID NO 23
<211> LENGTH: 238
<212> TYPE: PRT
<213> ORGANISM: Aequorea victoria

<400> SEQUENCE: 23
```

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

-continued

```
Gly Glu Gly Asp Ala Thr Tyr Gly Lys Leu Thr Leu Lys Phe Ile Cys
     35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65              70                  75                      80

His Asp Phe Phe Lys Ser Ala Met Pro Glu Gly Tyr Val Gln Glu Arg
             85                  90                      95

Thr Ile Phe Phe Lys Asp Asp Gly Asn Tyr Lys Thr Arg Ala Glu Val
            100                 105                110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145             150                 155                 160

Ile Lys Val Asn Phe Lys Ile Arg His Asn Ile Glu Asp Gly Ser Val
             165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
         195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235
```